(12) United States Patent
Stevens et al.

(10) Patent No.: US 10,844,004 B2
(45) Date of Patent: *Nov. 24, 2020

(54) SOLABEGRON ZWITTERION AND USES THEREOF

(71) Applicant: VELICEPT THERAPEUTICS, INC., Wayne, PA (US)

(72) Inventors: Raymond E. Stevens, West Chester, PA (US); Dalian Zhao, Fanwood, NJ (US); Bingidimi Itute Mobele, Altamont, NY (US)

(73) Assignee: Velicept Therapeutics, Inc., Wayne, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/246,114

(22) Filed: Jan. 11, 2019

(65) Prior Publication Data

US 2019/0185414 A1    Jun. 20, 2019

Related U.S. Application Data

(60) Continuation of application No. 16/018,945, filed on Jun. 26, 2018, now Pat. No. 10,221,126, which is a division of application No. 15/332,956, filed on Oct. 24, 2016, now Pat. No. 10,065,922.

(60) Provisional application No. 62/245,656, filed on Oct. 23, 2015, provisional application No. 62/245,670, filed on Oct. 23, 2015, provisional application No. 62/345,327, filed on Jun. 3, 2016, provisional application No. 62/345,357, filed on Jun. 3, 2016, provisional application No. 62/345,574, filed on Jun. 3, 2016.

(51) Int. Cl.
| | |
|---|---|
| *C07C 229/52* | (2006.01) |
| *A61K 31/196* | (2006.01) |
| *A61K 45/06* | (2006.01) |
| *C07C 227/16* | (2006.01) |
| *C07D 233/26* | (2006.01) |
| *C07D 498/04* | (2006.01) |

(52) U.S. Cl.
CPC .......... *C07C 229/52* (2013.01); *A61K 31/196* (2013.01); *A61K 45/06* (2013.01); *C07C 227/16* (2013.01); *C07D 233/26* (2013.01); *C07D 498/04* (2013.01); *C07B 2200/13* (2013.01)

(58) Field of Classification Search
CPC .. C07C 229/52; A61K 31/196; C07B 2200/13
See application file for complete search history.

(56) References Cited

U.S. PATENT DOCUMENTS

| | | |
|---|---|---|
| 4,478,849 A | 10/1984 | Ainsworth et al. |
| 4,772,631 A | 9/1988 | Holloway et al. |
| 6,069,176 A | 5/2000 | Tsuchiya et al. |
| 6,123,961 A | 9/2000 | Aberg |
| 6,228,398 B1 | 5/2001 | Devane et al. |
| 6,251,925 B1 | 6/2001 | Donaldson et al. |
| 6,398,762 B1 | 6/2002 | Vetter et al. |
| 6,444,685 B1 | 9/2002 | Sum et al. |
| 6,451,814 B1 | 9/2002 | Ashwell et al. |
| 6,548,523 B2 | 4/2003 | Lawrence et al. |
| 7,022,716 B2 | 4/2006 | Hu et al. |
| 7,034,053 B2 | 4/2006 | Deaton et al. |
| 7,425,639 B2 | 9/2008 | Cooke et al. |
| 7,709,677 B2 | 5/2010 | Cooke et al. |
| 8,017,613 B2 | 9/2011 | Scilimati et al. |
| 8,247,415 B2 | 8/2012 | Berger et al. |
| 8,354,403 B2 | 1/2013 | Edmondson et al. |
| 8,399,408 B2 | 3/2013 | Austen et al. |
| 8,399,480 B2 | 3/2013 | Berger et al. |
| 8,642,661 B2 | 2/2014 | Caltabiano et al. |
| 9,522,129 B2 | 12/2016 | Caltabiano et al. |
| 9,907,767 B2 | 3/2018 | Caltabiano et al. |
| 9,956,194 B2 | 5/2018 | Ohlstein et al. |
| 2003/0082230 A1 | 5/2003 | Baichwal et al. |
| 2004/0122014 A1 | 6/2004 | Mammen et al. |
| 2005/0101607 A1 | 5/2005 | Michel et al. |
| 2005/0137236 A1* | 6/2005 | Hattori .................. C07C 229/38 514/357 |
| 2005/0154041 A1 | 7/2005 | Michel et al. |
| 2005/0181031 A1 | 8/2005 | Saito et al. |
| 2005/0261328 A1 | 11/2005 | Wienrich et al. |

(Continued)

FOREIGN PATENT DOCUMENTS

| | | |
|---|---|---|
| CA | 2507343 A1 | 7/2005 |
| EP | 0400519 A1 | 12/1990 |

(Continued)

OTHER PUBLICATIONS

International Search Report and Written Opinion for PCT/US2017/036016 dated Aug. 28, 2017.

Uehling et al., "Biarylaniline Phenethanolamines as Potent and Selective β3 Adrenergic Receptor Agonist," J. Med. Chem, 2006, pp. 2758-2771.

Abrams et al. "Combination treatment with mirabegron and solifenacin in patients with overaactive bladder (OAB) efficacy results from a phase 2 study (Symphony)" May 4-8, 2013 AUA Annual Meeting, San Diego, CA (abstract only).

Arch et al. "Atypical ß0adrenoceptor on brown adipocytes as target for anti-obesity drugs" May 10, 1984, Nature 309:163-165.

(Continued)

*Primary Examiner* — Alicia L Otton
(74) *Attorney, Agent, or Firm* — Troutman Pepper Hamilton Sanders LLP

(57) ABSTRACT

This application relates to solabegron zwitterion useful for the treatment of lower urinary tract symptoms such as, for example, overactive bladder and prostate disorders. Additionally, this application relates to pharmaceutical compositions and methods of treatment utilizing the solabegron zwitterion for treating lower urinary tract symptoms. This application also relates to methods of preparing solabegron hydrochloride from the solabegron zwitterion.

13 Claims, 16 Drawing Sheets

(56) References Cited

U.S. PATENT DOCUMENTS

| | | |
|---|---|---|
| 2005/0261369 A1 | 11/2005 | Mehlburger et al. |
| 2006/0084700 A1 | 4/2006 | Michel |
| 2006/0240105 A1 | 10/2006 | Devane et al. |
| 2007/0078181 A1 | 4/2007 | Michel |
| 2009/0253705 A1 | 10/2009 | Berger et al. |
| 2010/0240697 A1 | 9/2010 | Suzuki et al. |
| 2010/0286275 A1 | 11/2010 | Zhang |
| 2010/0291209 A1 | 11/2010 | Vergnault et al. |
| 2011/0028461 A1 | 2/2011 | Berger et al. |
| 2011/0028481 A1 | 2/2011 | Berger et al. |
| 2011/0065660 A1 | 3/2011 | Baron et al. |
| 2011/0081426 A1 | 4/2011 | Rao et al. |
| 2012/0035118 A1 | 2/2012 | Caltabiano et al. |
| 2012/0053181 A1 | 3/2012 | Lin et al. |
| 2012/0142725 A1 | 6/2012 | Van Charldorp et al. |
| 2012/0157432 A1 | 6/2012 | Edmondson et al. |
| 2012/0202819 A1 | 8/2012 | Edmondson et al. |
| 2012/0225886 A1 | 9/2012 | Edmondson et al. |
| 2012/0258963 A1 | 10/2012 | Berger et al. |
| 2012/0289565 A1 | 11/2012 | Paborji et al. |
| 2013/0053403 A1 | 2/2013 | Berger et al. |
| 2013/0150402 A1 | 6/2013 | Suzuki et al. |
| 2013/0172277 A1 | 7/2013 | Caltabiano et al. |
| 2014/0243544 A1 | 8/2014 | Wang et al. |
| 2015/0306170 A1 | 10/2015 | Ahuja et al. |
| 2016/0158176 A1 | 6/2016 | Ohlstein et al. |
| 2017/0035716 A1 | 2/2017 | Ohlstein |
| 2017/0114005 A1 | 4/2017 | Stevens et al. |
| 2017/0151199 A1 | 6/2017 | Caltabiano et al. |
| 2017/0348263 A1 | 12/2017 | Ohlstein et al. |
| 2017/0348288 A1 | 12/2017 | Ohlstein et al. |
| 2018/0147169 A1 | 5/2018 | Caltabiano et al. |

FOREIGN PATENT DOCUMENTS

| | | |
|---|---|---|
| EP | 0455006 A2 | 11/1991 |
| EP | 0543662 A2 | 5/1993 |
| EP | 0806948 B1 | 9/2000 |
| EP | 1258253 A1 | 11/2002 |
| EP | 1967202 A1 | 9/2009 |
| EP | 2216021 A1 | 8/2010 |
| GB | 940540 A | 10/1963 |
| JP | 2006509752 A | 3/2006 |
| WO | 1995033724 A1 | 12/1995 |
| WO | 1999065877 A1 | 12/1999 |
| WO | 2001042195 A1 | 6/2001 |
| WO | 2001054728 A1 | 8/2001 |
| WO | 2003024483 A1 | 3/2003 |
| WO | 2004041806 A2 | 5/2004 |
| WO | 2004047838 A2 | 6/2004 |
| WO | 2005065673 A1 | 7/2005 |
| WO | 2005067938 A1 | 7/2005 |
| WO | 2006113649 A1 | 10/2006 |
| WO | 2008107446 A1 | 9/2008 |
| WO | 2008121268 A1 | 10/2008 |
| WO | 2008122014 A1 | 10/2008 |
| WO | 2009057685 A1 | 5/2009 |
| WO | 2009124167 A1 | 10/2009 |
| WO | 2010118291 A2 | 10/2010 |
| WO | 2011025690 A1 | 3/2011 |
| WO | 2011043942 A1 | 4/2011 |
| WO | 2011075514 A1 | 6/2011 |
| WO | 2011084456 A1 | 7/2011 |
| WO | 2011084459 A1 | 7/2011 |
| WO | 2012018773 A1 | 2/2012 |
| WO | 2013119910 A1 | 8/2013 |
| WO | 2014034860 A1 | 3/2014 |
| WO | 2015120110 A2 | 8/2015 |
| WO | 2016004056 A1 | 1/2016 |
| WO | 2016090168 A1 | 6/2016 |
| WO | 2017070689 A2 | 4/2017 |
| WO | 2017210696 A1 | 12/2017 |
| WO | 2017210700 A1 | 12/2017 |

OTHER PUBLICATIONS

Bianchetti et al. "In vitro inhibition of intestinal motiliy by phenylethanolaminotetralines: evidence of atypical ß-adrenoceptors in rat colon" Aug. 1990, Br. J. Pharmacol. 100:831-839.

Biers et al., The effects of a new selective ß3-adrenoceptor agonist (GW427353) on spontaneous activity and detrusor relaxation in human bladder, Journal Compilation, 2006 BJU International (2006), 98:1310-1314.

clinical trials.gov "Alternating Thalidomide and Lenalidomide Plus Rituximab as Initial Treatment for CLL" NCT01779167 May 17, 2010 (retrieved on Aug. 12, 2017). Retrieved from the internet; URL: < https://clinicaltrials.gov/archive/NCT0112,5176/2010_05_17> pp. 1-4; p. 1, brief summary and detailed description.

Definition of "compound" and "composition" from the Grant & Hackh's Chemical Dictionary, 1987, McGraw-Hill, Inc., p. 148.

Ellsworth et al. "Solabegron: a Potential Future Addition to the beta-3 Adrenoceptor Agonist Armamentarium for the Management of Overactive Bladder" (Mar. 5, 2015) Expert Opinion on Investig. Drugs 24(3):413-419.

Emorine et al. "Molecular characterization of the human beta 3-adrenergic receptor" Sep. 8, 1989, Science 245(4922):1118-1121.

Extended European Search Report for PCT/US2015/063795 dated Apr. 9, 2018.

Gillespie et al. "Modulation of non-voiding activity by the muscarinergic antagonist tolterodine and the Beta-3-adrenoceptor agonist mirabegron in conscious rats with partial outflow obstruction" 2012, BJU International 110:E132-E142.

Grudell et al. "Dose-response Effect of a beta3-adrenergic Receptor Agonist, Solabegron, on Gastrointestinal Transit, Bowel Function, and Somatostatin Levels in Health" May 1, 2008, Am. J. Physiol.-Gastro. Liver Physiol. 294(5):G1114-G1119.

Hertzberg et al. "Synthesis of the ß3-adrenergic Receptor Agonist Solabegron and Analogous N-(2-ethylamino)-ß-amino Alcohols From O-Acylated Cyanohydrins—Expanding the Scope of Minor Enantiomer Recycling" (Feb. 17, 2015) J. Organic Chem. 80(5):2937-2941.

Hicks, Alexander, et al. "GW427353 (solabegron), a novel, selective beta(3)-Adrenergic receptor agonist, evokes blader relaxation and increases micturition reflex threshold in the dog", Journal of Pharmacology and Experimental Therapeutics, vol. 323, No. 1, Oct. 2007, pp. 202-209, URL, XP000002658787, ISSN: 0022-3565.

Hutchinson et al. "ß3-Adrenoceptor regulation and relaxation responses in mouse ileum" 2000, Br. J. Pharmacol. 129:1251-1259.

International International Search Report and Written Opinon for PCT/US2017/036016 dated Aug. 28, 2017.

International Search Report and Written Opinion for PCT/US2011/046208 dated Sep. 26, 2011.

IInternational Search Report and Written Opinion for PCT/US2013/025285 dated Mar. 25, 2013.

International Search Report and Written Opinion for PCT/US2015/063795 dated Feb. 11, 2016.

International Search Report and Written Opinion for PCT/US2016/058516 dated Jun. 5, 2017.

International Search Report and Written Opinion for PCT/US2015/038583 dated Sep. 17, 2015.

International Search Report and Written Opinion for PCT/US2017/036005 dated Aug. 29, 2017.

Irwin et al., Prevalence, Severity, and Symptom Bother of Lower Urinary Tract Symptoms among Men in the EPIC Study: Impact of Overactive Bladder, European Urology (Mar. 3, 2009), 56:14-20.

Leach et al. "Structure-Function Studies of Muscarinic Acetylcholine Receptors" (2012) Handb. Exp. Pharmacol. 208:29-48.

Lee, J et al."Effects of Food Intake on the Pharmacokinetic Properties of Mirabegron Oral 5, 10-18 Controlled-Absorption System: A Single Dose, Randomized, Crossover Study in Healthy Adults" Clinical Therapeutics 2013, vol. 35, No. 3, pp. 333-341; pp. 334, left column, second-third paragraphs; p. 335, left column, third paragraph; p. 337.

Ma "Gynecological Urology", ed. Science Press, Aug. 2009, Edition 1, pp. 323-330.

(56) References Cited

OTHER PUBLICATIONS

NCT00501267: "A Study to Test the Interaction of Two Medications for the Treatment of Overactive Bladder" available at <https://clinicaltrials.gov/ct2/show/NCT00501267?term=NCT00501267&rank=1> (as retrieved on Feb. 15, 2016).

Ohlstein et al., A Multicenter, Double-blind, Randomized, Placebo-controlled Trial of the beta3-Adrenoceptor Agonist Solabegron for Overactive Bladder, European Urology (Jun. 5, 2012), 62:834-840.

Otsuka et al. "Combination Effect of B3-Adrenoceptor Agonist and Muscarinic Receptor Antagonist on Human Detrusor Muscle Relaxation in Vitro" Oct. 2012, International Continence Society Meeting, pp. 894-895.

Product Label for Myrbetriq™ (mirabegron) Jun. 2012.

Product Label for VESIcarTM (solifenacin succinate) Apr. 2010.

Rackley et al. "Nighttime Dosing with Tolterodine Reduces Overactive Bladder-Related Nocturnal Micturitions in Patients with Overactive Bladder and Nocturia" 2006, Urology 67:731-736.

Singapore Search Report for SG 11201404776P dated Jul. 8, 2015.

Vrydag et al. "Do gene polymorphisms alone or in combination affect the function of human ß-adrenoceptors?" 2009, Br. J. Pharmacol. 156:127-134.

Kajoika et al. "Etiology of overactive bladder and its therapeutic perspective—focusing on a myogenic basis for the overactive bladder" Fukuoka Acta Medica, 2010, vol. 101, No. 5 , p. 94-100.

Japanese (1st) Office Action, for Japanese Patent Application No. 2017-548369 dated Sep. 10, 2019.

\* cited by examiner

| EXP. | SAMPLE DESCRIPTION | PLM IMAGE |
|---|---|---|
| EXPERIMENT 3, PROCEDURE A FORM II | POST SEEDING | |
| | FINAL SLURRY | |
| | DRY SOLIDS | |

FIGURE 6-2

| EXP. | SAMPLE DESCRIPTION | PLM IMAGE |
|---|---|---|
| EXPERIMENT 3, PROCEDURE B FORM II | POST SEEDING | |
| | FINAL SLURRY | |

FIGURE 6-3

SLURRY CONDITIONING CONDITIONS AND RESULTS FOR RELATIVE STABILITY EVALUATION OF ZI FORMS I AND II

| INPUT ZI FORM | IPA:H2O V/V | 1ST STEP | | 2ND STEP | | FINAL ZI FORM BY XRPD |
|---|---|---|---|---|---|---|
| | | TEMPERATURE °C | TIME H | TEMPERATURE °C | TIME H | |
| I | 30/70 | 20 | 40 | 55 | 30 | II |
| I | 40/60 | 20 | 40 | 55 | 30 | II |
| I | 45/55 | 20 | 40 | 55 | 30 | II |
| I | 50/50 | 20 | 40 | 55 | 30 | II |
| I+II | 30/70 | 20 | 40 | 55 | 30 | II |
| I+II | 40/60 | 20 | 40 | 55 | 30 | II |
| I+II | 45/55 | 20 | 40 | 55 | 30 | II |
| I+II | 50/50 | 20 | 40 | 55 | 30 | II |

FIGURE 10

| ZI FORM & PURITY | DESCRIPTION | PLM IMAGE |
|---|---|---|
| FORM I 95.6 A% | AFTER ADDING 2% SEED OF HCl SALT |  |
| | FINAL BATCH SLURRY |  |
| FORM II 99.4 A% | FINAL BATCH SLURRY |  |
| | FINAL DRY SOLIDS |  |

PEAK LIST FOR SOLABEGRON ZWITTERION FORM I

| NO. | 2-THETA (DEG) | RELATIVE PEAK INTENSITY | RELATIVE PEAK HEIGHT |
|---|---|---|---|
| 1 | 6.2 | 100.0 | 100.0 |
| 2 | 10.5 | 0.5 | 0.8 |
| 3 | 12.5 | 21.0 | 22.0 |
| 4 | 15.1 | 1.2 | 1.5 |
| 5 | 16.9 | 2.1 | 2.3 |
| 6 | 18.0 | 0.8 | 1.2 |
| 7 | 18.6 | 5.9 | 6.2 |
| 8 | 18.8 | 15.2 | 15.0 |
| 9 | 19.3 | 1.7 | 1.8 |
| 10 | 20.6 | 37.2 | 37.1 |
| 11 | 21.1 | 4.2 | 3.7 |
| 12 | 21.5 | 2.7 | 2.9 |
| 13 | 22.3 | 5.4 | 2.8 |
| 14 | 22.5 | 1.4 | 2.2 |
| 15 | 22.9 | 1.8 | 2.1 |
| 16 | 23.8 | 1.0 | 1.5 |
| 17 | 25.2 | 16.0 | 12.6 |
| 18 | 26.6 | 2.3 | 1.4 |
| 19 | 27.4 | 0.5 | 0.8 |
| 20 | 28.2 | 0.7 | 1.0 |
| 21 | 29.6 | 1.0 | 1.4 |
| 22 | 30.9 | 0.6 | 0.9 |
| 23 | 31.9 | 0.9 | 1.2 |
| 24 | 32.9 | 2.7 | 3.0 |
| 25 | 34.4 | 0.7 | 0.9 |
| 26 | 36.2 | 1.0 | 1.3 |
| 27 | 36.8 | 0.7 | 0.9 |
| 28 | 38.2 | 1.3 | 1.9 |
| 29 | 39.3 | 1.6 | 1.2 |

FIGURE 13

PEAK LIST FOR SOLABEGRON ZWITTERION FORM II

| NO. | 2-THETA (DEG) | RELATIVE PEAK INTENSITY | RELATIVE PEAK HEIGHT |
|---|---|---|---|
| 1 | 6.1 | 13.1 | 18.1 |
| 2 | 7.5 | 16.9 | 19.8 |
| 3 | 9.4 | 29.2 | 36.0 |
| 4 | 11.3 | 18.4 | 24.7 |
| 5 | 12 | 4.3 | 7.5 |
| 6 | 13.6 | 7.5 | 10.5 |
| 7 | 14.5 | 12.3 | 9.5 |
| 8 | 15.1 | 25.0 | 31.1 |
| 9 | 16.2 | 27.1 | 22.3 |
| 10 | 17.6 | 62.6 | 38.7 |
| 11 | 17.8 | 9.1 | 15.0 |
| 12 | 18.7 | 57.7 | 64.3 |
| 13 | 19.6 | 47.9 | 59.6 |
| 14 | 20.1 | 100.0 | 100.0 |
| 15 | 20.5 | 62.8 | 84.2 |
| 16 | 21.8 | 38.0 | 27.5 |
| 17 | 22.6 | 27.8 | 29.0 |
| 18 | 23.1 | 5.3 | 9.9 |
| 19 | 23.7 | 57.7 | 52.5 |
| 20 | 24.8 | 36.3 | 28.1 |
| 21 | 25.8 | 84.7 | 86.0 |
| 22 | 27.2 | 5.0 | 7.4 |
| 23 | 27.5 | 6.9 | 4.1 |
| 24 | 28.9 | 35.2 | 20.6 |
| 25 | 35.9 | 8.7 | 12.7 |
| 26 | 39.2 | 12.7 | 11.3 |

FIGURE 14

SOLABEGRON ZWITTERION AND USES THEREOF

CROSS-REFERENCE TO RELATED APPLICATIONS

The present application is a continuation application of U.S. application Ser. No. 16/018,945, filed Jun. 26, 2018 entitled "Solabegron Zwitterion and Uses Thereof", which is a divisional application of U.S. application Ser. No. 15/332,956, filed Oct. 24, 2016 entitled "Solabegron Zwitterion and Uses Thereof"; which claims the benefit of U.S. Provisional Application No. 62/245,656, filed Oct. 23, 2015; U.S. Provisional Application No. 62/245,670, filed Oct. 23, 2015; U.S. Provisional Application No. 62/345,327, filed Jun. 3, 2016; U.S. Provisional Application No. 62/345,357, filed Jun. 3, 2016; and U.S. Provisional Application No. 62/345,574, filed Jun. 3, 2016 the disclosures of which are hereby incorporated by reference in their entirety.

SUMMARY

Embodiments of this application relate to processes for the preparation of the β-3-adrenoceptor agonist solabegron, and compounds useful in the processes for the preparation of solabegron and compositions comprising compounds useful for therapeutic purposes.

β-adrenoceptors belong to the family of adrenoceptors which mediate the physiological actions of the hormones adrenaline and noradrenaline. Such receptors have been described for example by J R S Arch et. al., Nature, 309, 163-165 (1984); C Wilson et. al., Eur. J. Pharmacol., 100, 309-319 (1984); L J Emorine et. al., Science, 245, 1118-1121 (1989); and A. Bianchetti et. al. Br. J. Pharmacol., 100, 831-839 (1990).

Phenethanolamine derivatives having activity at 3-adrenoceptors are disclosed in, for example, European Patent Applications EP-A-0455006 and EP-A-0543662.

Sub-types of the adrenoceptors, $\alpha_1$-, $\alpha_2$-, $\beta_1$-, $\beta_2$- and $\beta_3$- can be identified on the basis of their pharmacological properties and physiological effects. Chemical agents which stimulate or block these receptors (but not $\beta_3$) are widely used in clinical medicine. More recently, emphasis has been placed upon specific receptor selectivity in order to reduce side effects caused, in part, by interactions with other receptors.

β-adrenoceptors ($\beta_3$ and/or beta-3) are known to occur in adipose tissue and the gastrointestinal tract. Compounds having β-adrenoceptor agonist activity have also been described as being useful in the treatment of hyperglycemia; as being useful in the treatment of lower urinary tract symptoms such as, for example, overactive bladder and prostate disorders; as animal growth promoters; as blood platelet aggregation inhibitors; as positive inotropic agents; as antiatherosclerotic agents; and as being useful in the treatment of glaucoma.

A particularly useful beta-3 adrenoceptor agonist is 3'-[(2-{[(2R)-2-(3-chlorophenyl)-2-hydroxyethyl]amino}ethyl)amino]biphenyl-3-carboxylic acid (hereinafter "solabegron") Formula I:

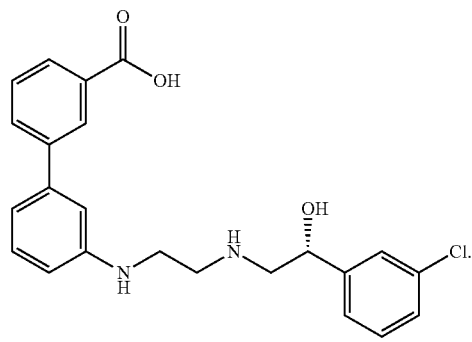

(Formula I)

Solabegron is described and claimed in U.S. Pat. No. 6,251,925 as a compound, pharmaceutical composition and method of treatment and described and claimed in U.S. Pat. No. 8,642,661 and United States Patent Publication No. 2013/0172277A1 as a combination therapy with an antimuscarinic agent. Additionally, Ohlstein, et. al. have demonstrated that solabegron significantly reduced the symptoms of OAB in women with moderate to severe OAB, showing that solabegron is safe, well tolerated, and does not demonstrate significant differences in adverse events as compared to placebo. Ohlstein, E. H., et al., A Multicenter, Double-Blind, Randomized, Placebo-controlled Trial of the 33-Adrenoceptor Agonist Solabegron for Overactive Bladder, Eur. Urol., 2012, 62(5), 834-40. U.S. Provisional Patent Application No. 62/020,889 describes a drug interaction study conducted in healthy human volunteers, using repeat oral doses of solabegron and oxybutynin administered singly as well as in combination with each other, in order to assess the effects on pharmacokinetic and pharmacodynamic parameters, as measured by post void residual (PVR) volumes.

In view of the above disclosed beneficial therapeutic properties of solabegron it is therefore desirable to produce solabegron on a larger scale. Unfortunately, the laboratory scale method for preparing solabegron disclosed in U.S. Pat. No. 6,251,925, while providing pharmaceutical quality material, is not amenable to production scale. Therefore a need exists for a large scale process for the production of pharmaceutical grade solabegron. In addition, a need exists for alternative forms of solabegron that may be useful in compositions for therapeutic purposes.

In one embodiment the present application describes a solid compound according to Formula II:

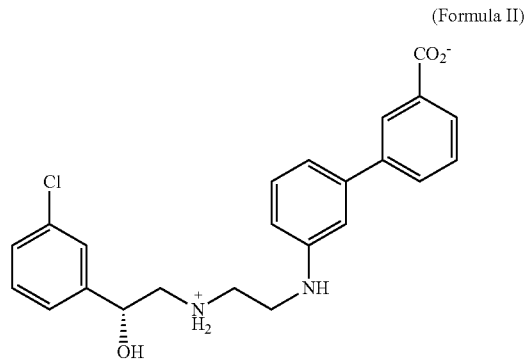

(Formula II)

or a pharmaceutically acceptable salt or a stereoisomer or a solvate or a polymorph thereof.

In one embodiment the present application describes a pharmaceutical composition comprising: a therapeutically effective amount of a compound according to Formula II:

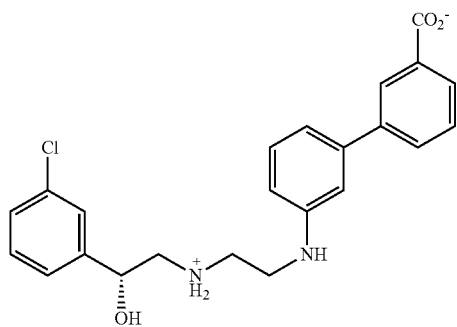

Formula II or a pharmaceutically acceptable salt or a stereoisomer or a solvate or a polymorph thereof; and at least one pharmaceutically acceptable carrier or excipient.

In one embodiment the present application describes a method for treating lower urinary tract symptoms (hereinafter "LUTS"), comprising administering a therapeutically effective amount of a compound according to Formula II or a pharmaceutically acceptable salt or a stereoisomer or a solvate or a polymorph thereof to a patient in need thereof. In another embodiment the present application describes a method for treating overactive bladder, comprising administering a therapeutically effective amount of a compound according to Formula II or a pharmaceutically acceptable salt or a stereoisomer or a solvate or a polymorph thereof to a patient in need thereof.

In one embodiment the present application describes a process for preparing solabegron hydrochloride salt according to Formula I-HCl

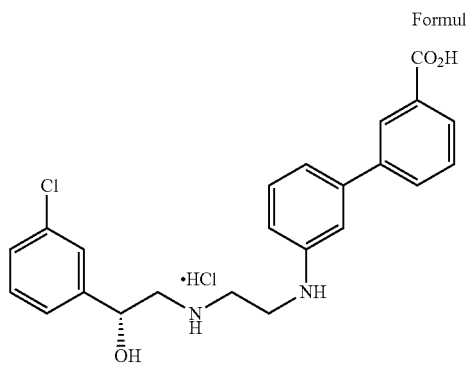

Formula I-HCl comprising contacting a zwitterion of Formula II

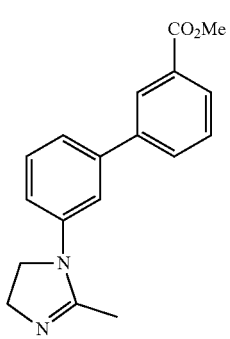

Formula II with hydrochloric acid.

In one embodiment the present application describes a process for preparing 3'-(2'methyl-4,5-dihydro-1H-imidazol-1-yl)-[1,1']biphenyl-3-carboxylate according to Formula IV

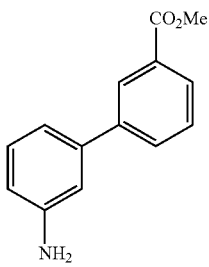

Formula IV or a pharmaceutically acceptable salt, stereoisomer, solvate or polymorph thereof, comprising: contacting the biphenyl amine intermediate according to Formula V

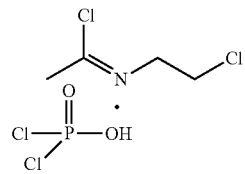

Formula V with the acetimidoyl chloride according to Formula VI

Formula VI wherein the acetimidoyl chloride according to Formula VI is generated in situ from the reaction of N-(2-chloroethyl) acetamide and phosphoryl chloride.

In one embodiment the present invention describes a compound according to Formula III

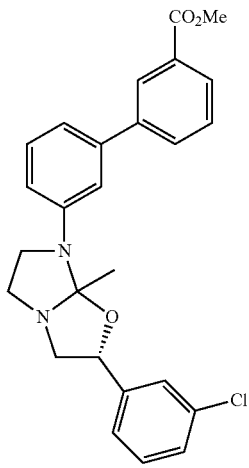

Formula III or a pharmaceutically acceptable salt, stereoisomer, solvate, or polymorph thereof.

In one embodiment the present invention describes a compound according to Formula IV

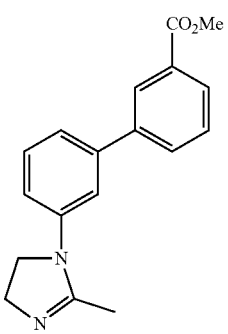

Formula IV or a pharmaceutically acceptable salt, stereoisomer, solvate, or polymorph thereof.

In one embodiment the present application describe a process for preparing solabegron zwitterion according to Formula II

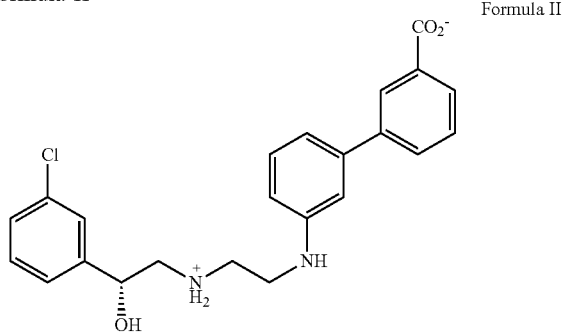

Formula II comprising contacting a solabegron sodium salt according to Formula I-Na

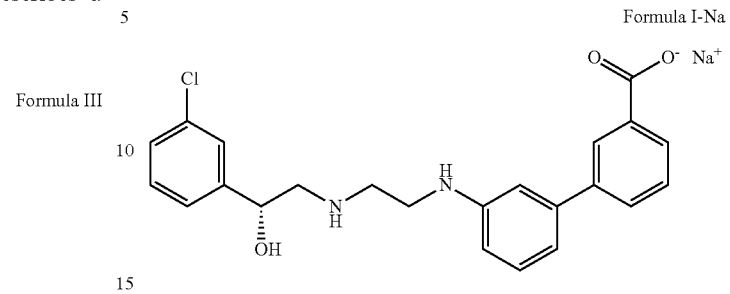

Formula I-Na with hydrochloric acid.

BRIEF DESCRIPTION OF THE FIGURES

FIG. 6-1 to 6-3—shows the crystal morphology by Polarizing Light Microscopy (PLM) of solabegron zwitterion, form I crystals; solabegron zwitterion, form II crystals obtained from Procedure A; and solabegron zwitterion, form II crystals obtained from Procedure B of Example 3.

FIG. 10—is a table which lists the testing conditions and results of the relative stability of solabegron zwitterion Forms I and II FIG. 11—is XRPD data of Form I of the solebegron HCl salt (bottom) against a standard of solebegron HCl salt FIG. 12—Shows PLM images of slurry samples from crystallization of solabegron HCl salt with feed solabegron zwitterion crystallized from crude solabegron sodium salt stock solution.

FIG. 13—is an XRPD peak list for the solabegron zwitterion, form I as measured on XRPD-1 Rigaku MiniFlex 600 (GMP instrument) under the experimental parameters: X-Ray tube Cu (Kα); tube voltage 40 kV; tube current 15 mA. Soller (Inc.) 2.5 deg.; IHS 10.0 mm; DS 1.250 deg.; SS 1.250 deg.; Soller (rec.) 2.5 deg.; RS 0.15 monochromatization Kβ filter (X1); Scan from 2 to 40 degrees 2-theta; 0.01 degrees/step; scan rate 2 degrees/min.

FIG. 14—is an XRPD peak list for the solabegron zwitterion, form II as measured on XRPD-1 Rigaku MiniFlex 600 (GMP instrument) under the experimental parameters: X-Ray tube Cu (Kα); tube voltage 40 kV; tube current 15 mA. Soller (Inc.) 2.5 deg.; IHS 10.0 mm; DS 1.250 deg.; SS 1.250 deg.; Soller (rec.) 2.5 deg.; RS 0.15 monochromatization Kβ filter (X1); Scan from 2 to 40 degrees 2-theta; 0.01 degrees/step; scan rate 2 degrees/min.

DETAILED DESCRIPTION

Figure 1:
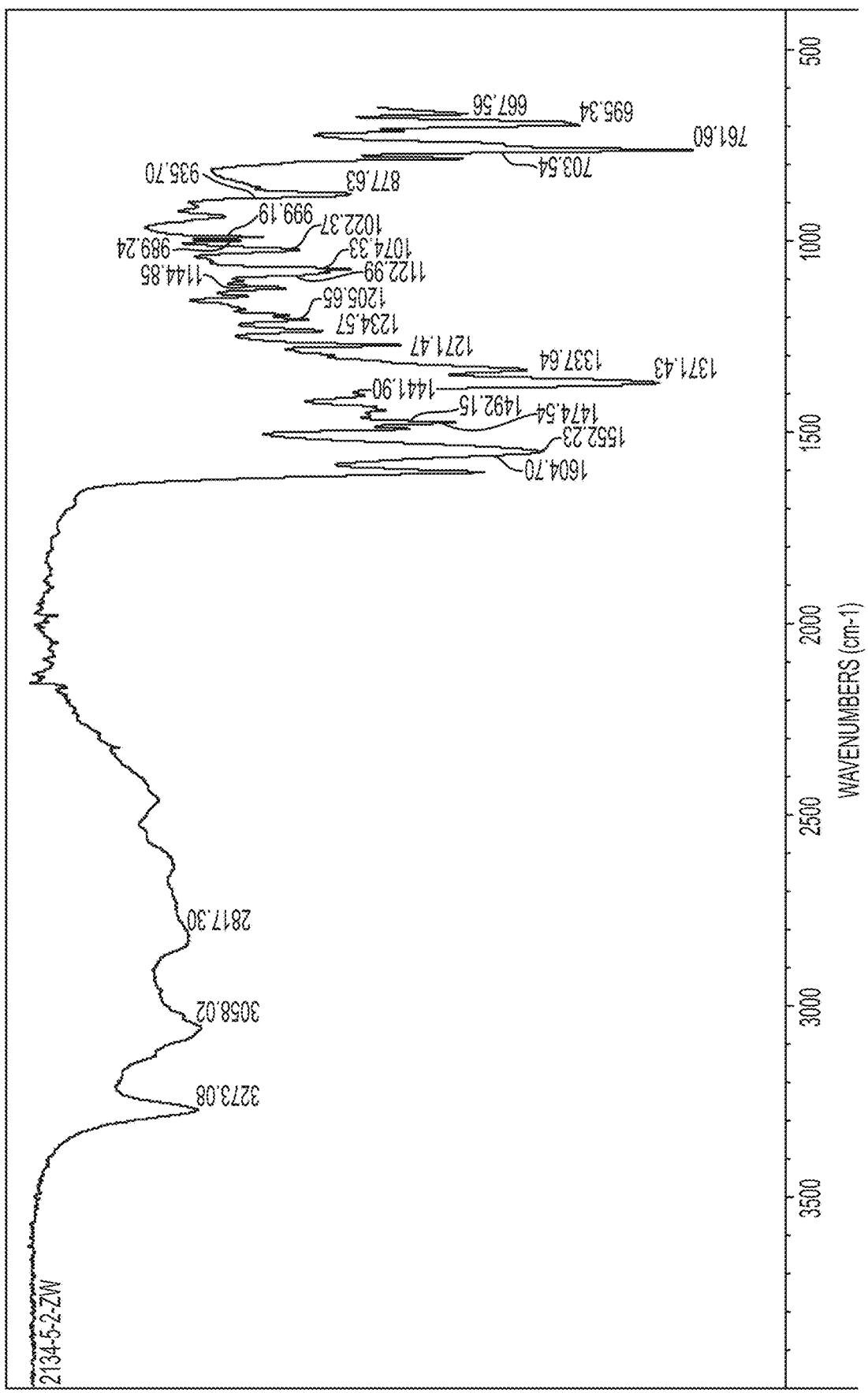
FIG. 1—is an FT-IR spectrum of the compound of Formula II, form I.
Figure 2:
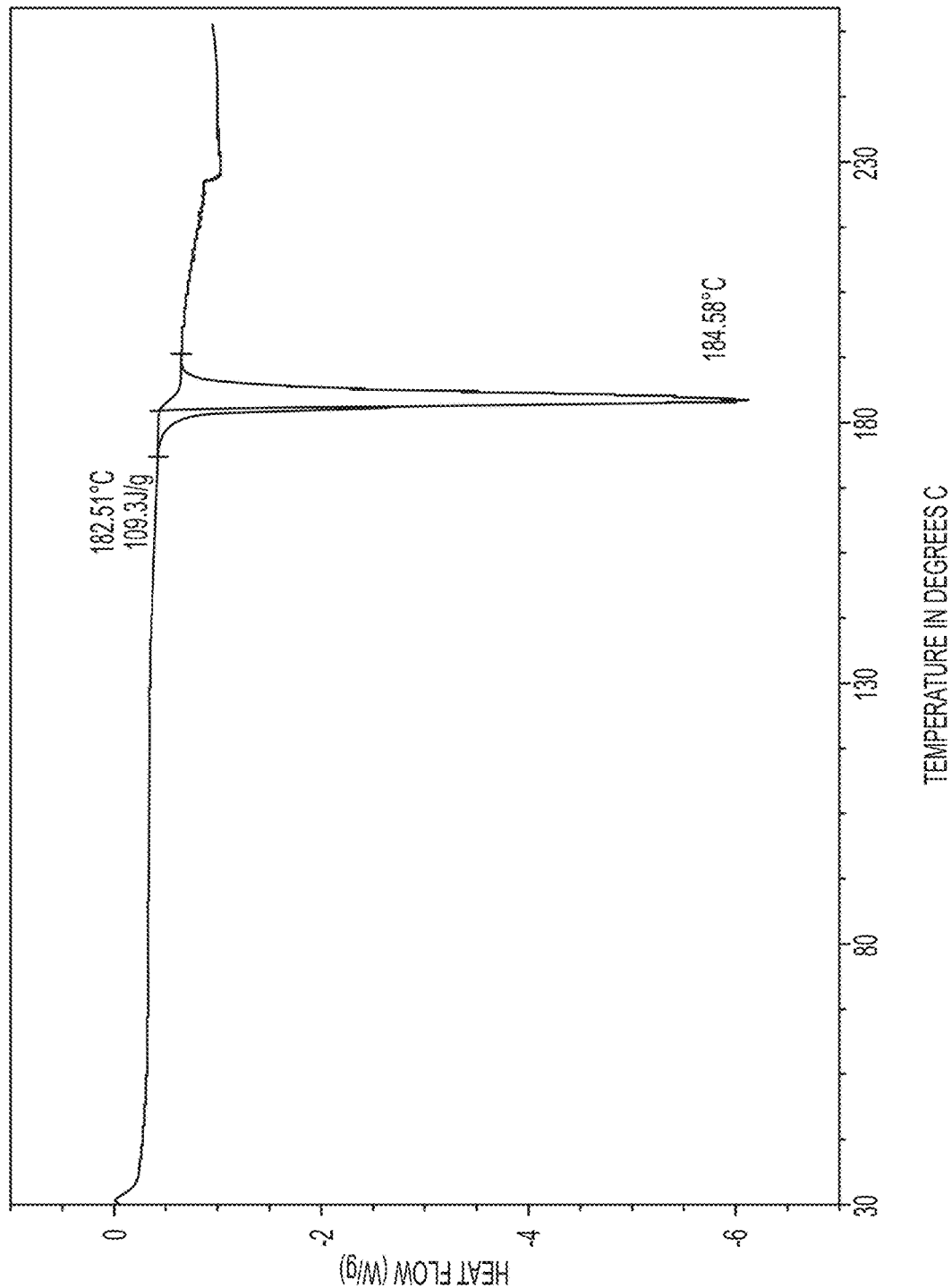
FIG. 2—is a Differential Scanning Calorimetry plot of the compound of Formula II, form I.
Figure 3:
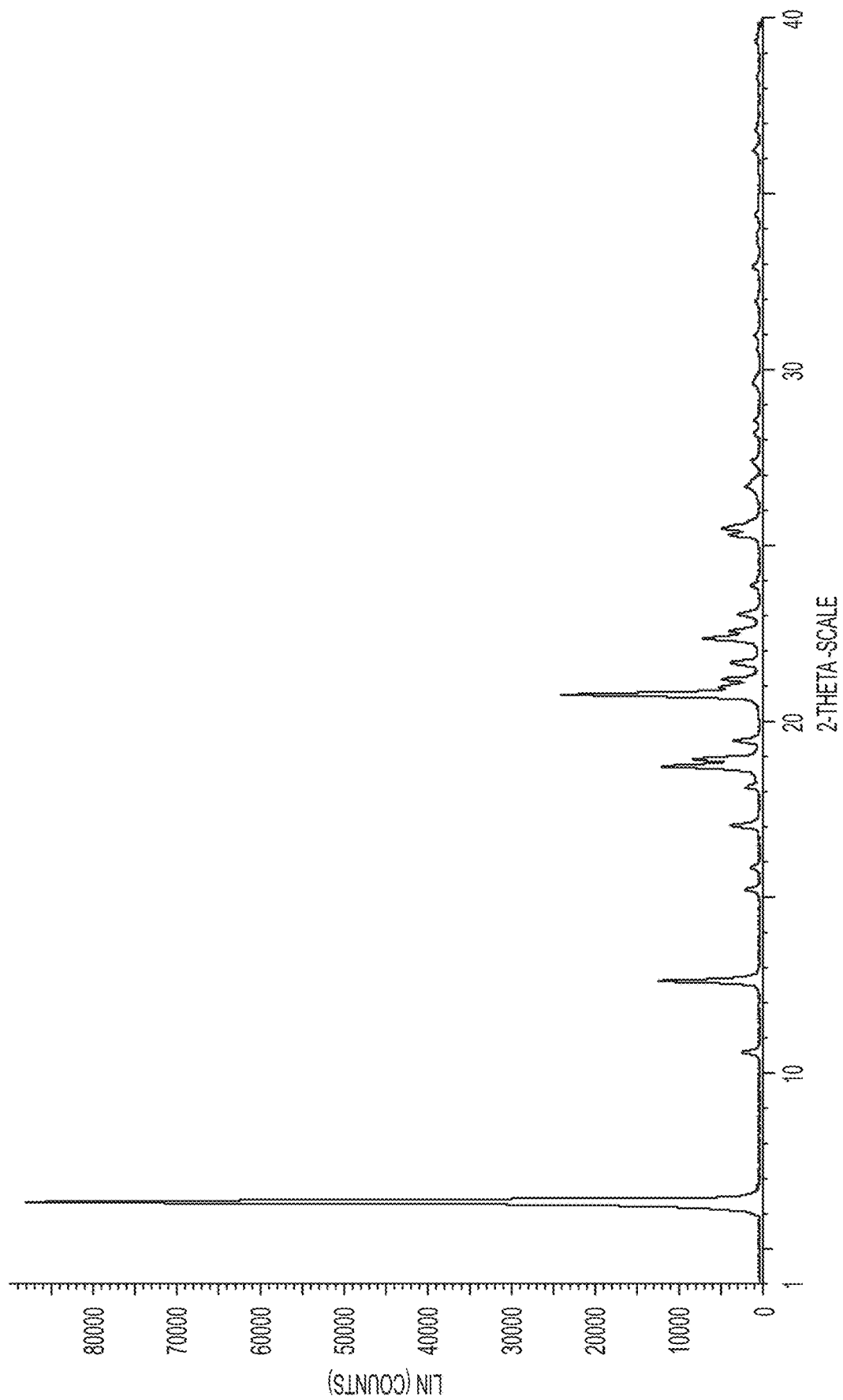
FIG. 3—shows an X-Ray Powder Diffraction Pattern of the compound of Formula II, form I.
Figure 4:
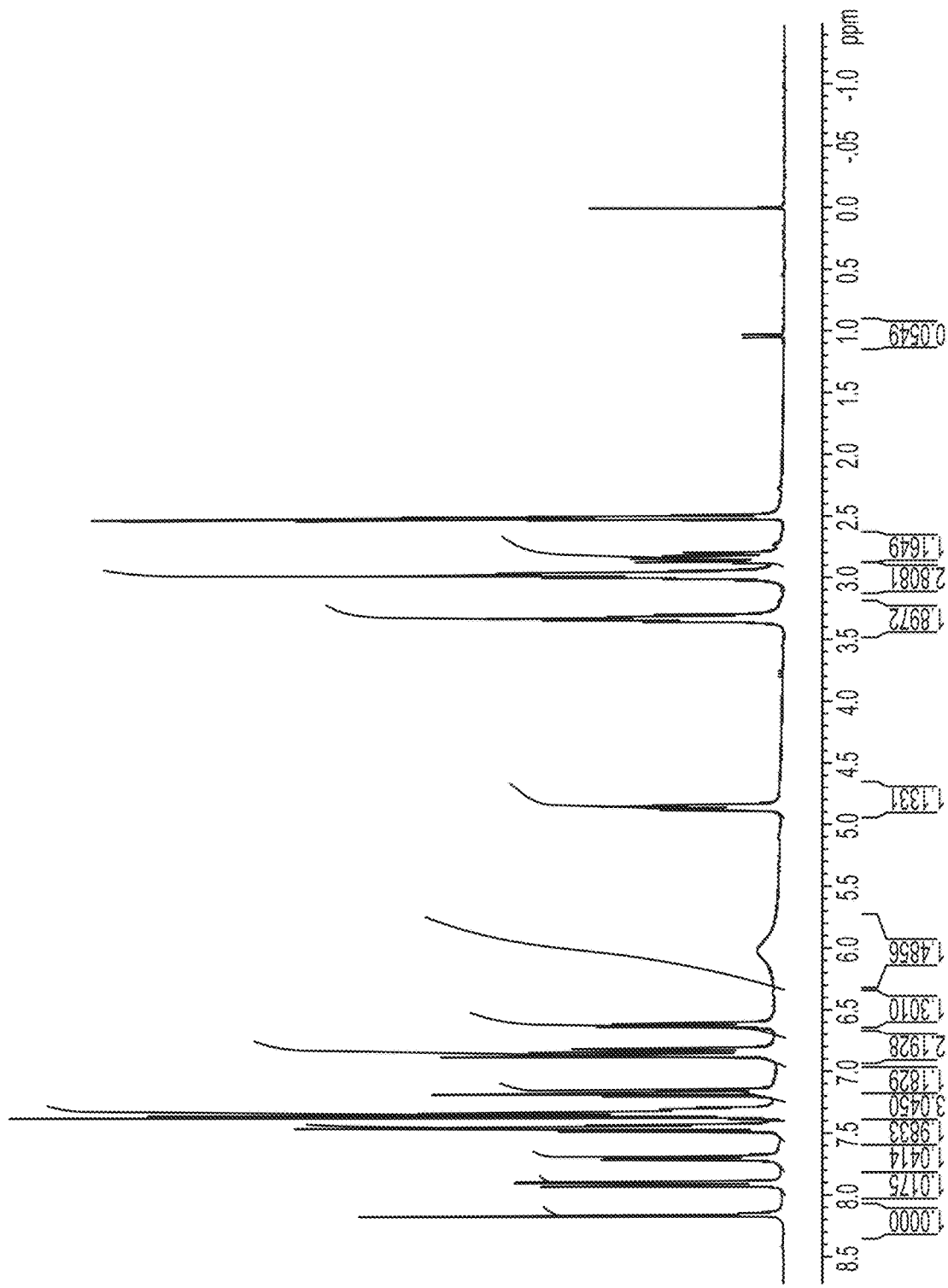
FIG. 4—is a $^1$H NMR spectrum of the compound of Formula II, form I.
Figure 5:
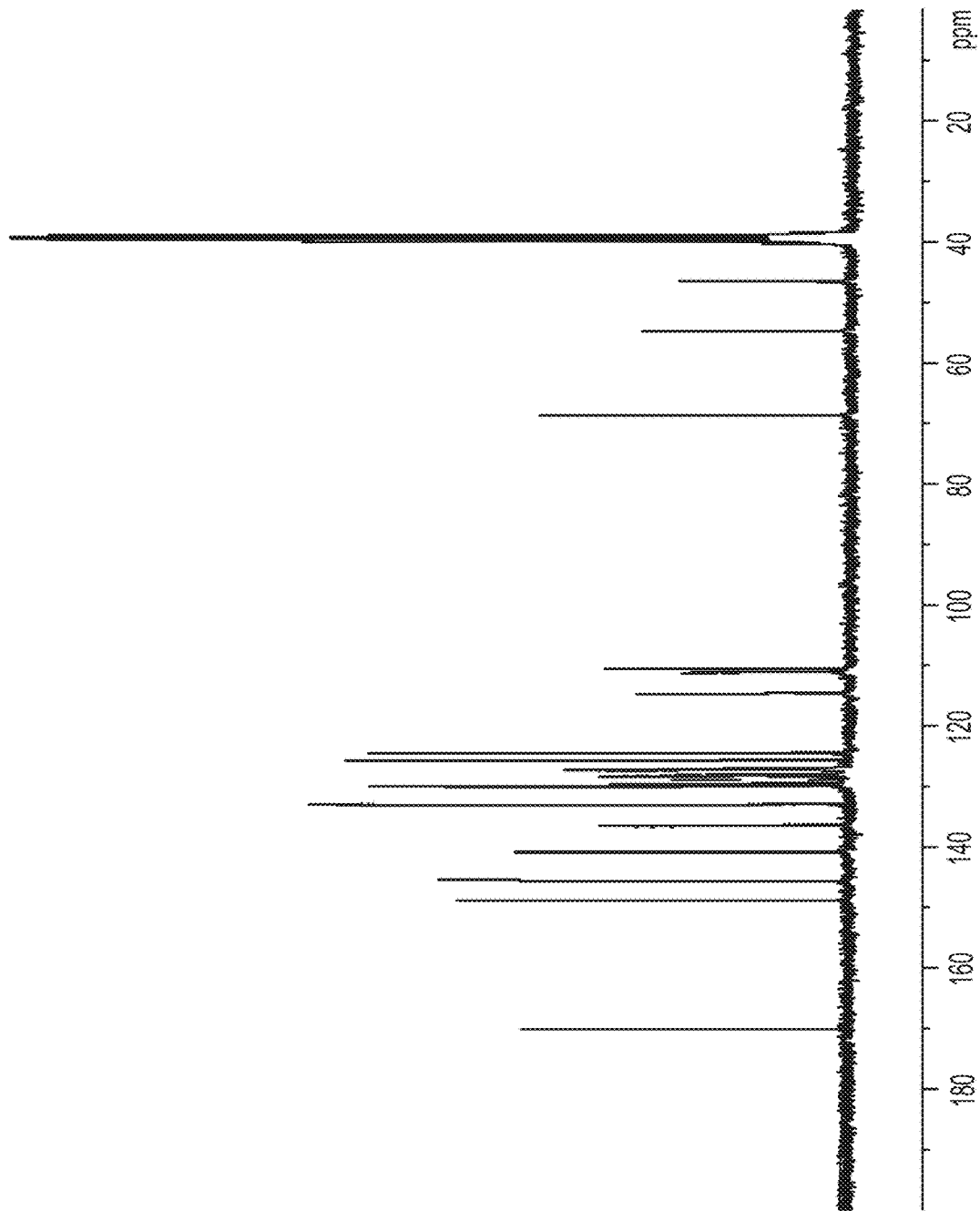
FIG. 5—is a $^{13}$C NMR spectrum of the compound of Formula II, form I.

The present application describes processes for the preparation of solabegron zwitterion (Formula II) and solabegron HCl salt (Formula I HCl):

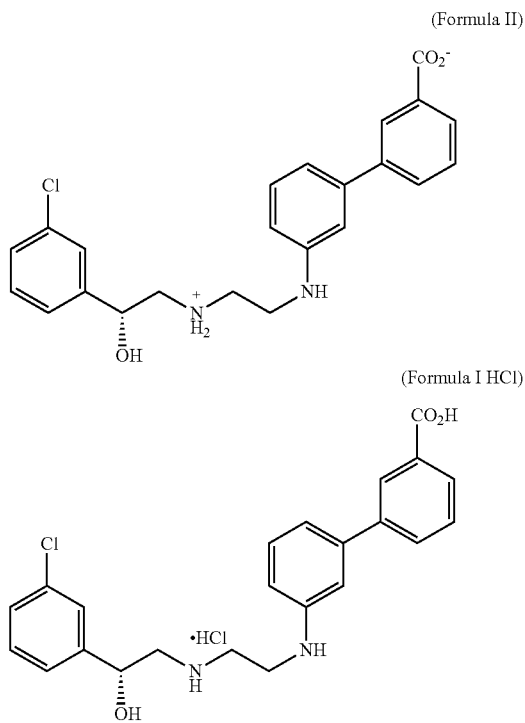

or a pharmaceutically acceptable salt, stereoisomer, solvate or polymorph thereof.

Additionally, described herein are compounds useful for the preparation of the solabegron HCl, solabegron zwitterion or a pharmaceutically acceptable salt, stereoisomer, solvate or a polymorph thereof.

In addition, described herein is the use of solabegron zwitterion as a therapeutically beneficial treatment for overactive bladder and LUTS.

Pharmaceutical compositions containing solabegron zwitterion as well as methods of treating overactive bladder and LUTS utilizing the solabegron zwitterion and the pharmaceutical compositions containing solabegron zwitterion are also described.

Definitions

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

As used herein, the term "about" means plus or minus 10% of a given value. For example, "about 50%" means in the range of 45%-55%.

As used herein the term "agonist" refers to a compound, the presence of which results in a biological activity of a receptor that is the same as the biological activity resulting from the presence of a naturally occurring ligand for the receptor.

The phrase "pharmaceutically acceptable" refers to molecular entities and compositions that are generally regarded as safe and nontoxic. In particular, pharmaceutically acceptable carriers, diluents or other excipients used in the pharmaceutical compositions of this application are physiologically tolerable, compatible with other ingredients, and do not typically produce an allergic or similar untoward reaction (e.g., gastric upset, dizziness and the like) when administered to a patient. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans. The phrase "pharmaceutically acceptable salt(s)", as used herein, includes those salts of compounds of the application that are safe and effective for use in mammals and that possess the desired biological activity. Pharmaceutically acceptable salts include salts of acidic or basic groups present in compounds of the application or in compounds identified pursuant to the methods of the application. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, genitsate, fumarate, gluconate, glucuronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the application can form pharmaceutically acceptable salts with various amino acids. Suitable base salts include, but are not limited to, aluminum, calcium, lithium, magnesium, potassium, sodium, zinc, iron and diethanolamine salts. Pharmaceutically acceptable base addition salts are also formed with amines, such as organic amines. Examples of suitable amines are N,N'-dibenzylethylenediamine, chloroprocaine, choline, diethanolamine, dicyclohexylamine, ethylenediamine, N-methylglucamine, and procaine.

As used herein the phrase "lower urinary tract symptoms" or "LUTS" refers to a group of medical symptoms, comprising increased frequency of urination, increased urinary urgency of urination, painful urination, excessive passage of urine at night, poor stream, overactive bladder, hesitancy, terminal dribbling, incomplete voiding and overflow incontinence.

As used herein the phrase "overactive bladder" or "OAB" refers to a group of medical symptoms, comprising urinary urgency, frequent urination, nocturia, urinating unintentionally and urge incontinence.

As used herein, the term "therapeutic" means an agent utilized to treat, combat, ameliorate, protect against or improve an unwanted condition or disease of a subject.

As used herein, the term "effective amount" refers to an amount that results in measurable inhibition of at least one symptom or parameter of a specific disorder or pathological process.

As used herein the term "therapeutically effective amount" of compositions of the application is a predetermined amount which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect or physician observes a change).

As used herein the terms "treat", "treated", or "treating" refer to both therapeutic treatment and prophylactic or preventative measures, wherein the object is to protect against (partially or wholly) or slow down (e.g., lessen or postpone the onset of) an undesired physiological condition, disorder or disease, or to obtain beneficial or desired clinical results such as partial or total restoration or inhibition in decline of a parameter, value, function or result that had or would become abnormal. For the purposes of this application, beneficial or desired clinical results include, but are not limited to, alleviation of symptoms; diminishment of the extent or vigor or rate of development of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease. Treatment seeks to elicit a clinically significant response without excessive levels of side effects.

As used herein the terms, "pulse", "pulses" "pulsed delivery" "pulsatile delivery device" refer to pharmaceutical compositions and methods of treatment wherein a therapeutic agent is delivered rapidly within a short period of time, as a result of a biological or external trigger, after a specific lag time.

As used herein the term "immediate release" refers to pharmaceutical compositions that release the active ingredient within a small period of time, typically less than 45 minutes.

As used herein the term "modified release" refers to pharmaceutical compositions that either release the active ingredient at a sustained and controlled release rate over a period of time such as, for example, 6 hours, 8 hours, 12 hours, 16 hours, and 24 hours or release the pharmaceutical dosage after a set time such as, for example, enteric-coated compositions that release the dosage in the intestinal track.

As used herein the terms "w/w", v/v" wt %" and "weight %" refer to weight percent and/or volume percent of the named molecule in solution.

As used herein a solid of solabegron zwitterion is meant to include both amorphous solids and crystalline solids.

Solabegron Zwitterion (Formula II)

In one embodiment the present application describes a compound according to Formula II:

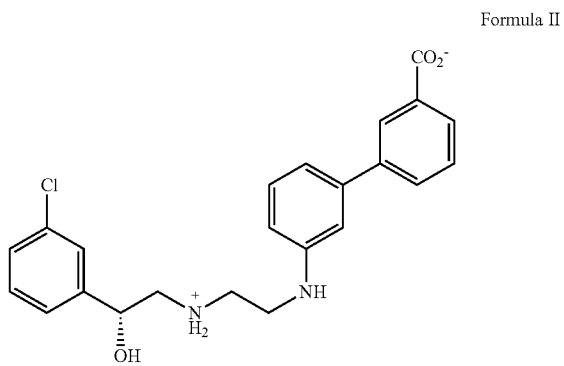

Formula II or a pharmaceutically acceptable salt, stereoisomer, solvate or polymorph. In some embodiments the compound of Formula II is a solid. In some embodiments the compound of Formula II is an amorphous solid. In further embodiments the compound of Formula II is a crystal or crystalline solid. In some embodiments the compound of Formula II is a single polymorph. In further embodiments the compound of Formula II is more than one polymorph. In some embodiments the compound of Formula II is an anhydrous solid or crystal. In further embodiments, the compound of Formula II is a solid or crystalline hydrate of isopropanol solvate. In some embodiments the compound of Formula II is characterized by a peak at 1552 cm$^1$ upon infrared analysis. In further embodiments the compound of Formula II is characterized by a peak at about 184° C. upon differential scanning calorimetry analysis. In further embodiments the compound of Formula II is characterized by peaks at about 67° C. (very broad), 131° C. (broad) and 180° C. upon differential scanning calorimetry analysis. In some embodiments the compound of Formula II is characterized by an x-ray powder diffraction pattern having peaks expressed in degrees 2θ (±2) at 6.3, 12.6; 18.6; 18.9; 20.9; 22.4; 25.3; and 25.5. In some embodiments the compound of Formula II is characterized by an x-ray powder diffraction pattern having peaks expressed in degrees 2θ (±2) at 6.2, 12.5; 18.8; 20.6; and 25.2. In some embodiments the compound of Formula II is characterized by an x-ray powder diffraction pattern having peaks expressed in degrees 2θ (±2) at 6.2, 12.5; 18.6; 18.8; 20.6; 22.3, and 25.2. In some embodiments the compound of Formula II is characterized by an x-ray powder diffraction pattern having peaks expressed in degrees 2θ (±2) at 6.2, 12.5; 16.9, 18.6; 18.8; 20.6; 21.1, 21.5; 22.3, 25.2; 26.6, and 32.9. In some embodiments the compound of Formula II is characterized by an x-ray powder diffraction pattern having peaks expressed in degrees 2θ (±2) at 17.6, 18.7, 19.6, 20.1, 20.5, 23.7, and 25.8. In some embodiments the compound of Formula II is characterized by an x-ray powder diffraction pattern having peaks expressed in degrees 2θ (±2) at 9.4, 15.1, 16.2, 17.6, 18.7, 19.6, 20.1, 20.5, 21.8, 22.6, 23.7, 24.8, 25.8, and 28.9. In some embodiments the compound of Formula II is characterized by an x-ray powder diffraction pattern having peaks expressed in degrees 2θ (±2) at 6.1, 7.5, 9.4, 11.3, 14.5, 15.1, 16.2, 17.6, 18.7, 19.6, 20.1, 20.5, 21.8, 22.6, 23.7, 24.8, 25.8, and 28.9. In further embodiments the compound of Formula II, is characterized by $^1$H NMR peaks ($^1$H NMR, 300 MHz, DMSO-d$_6$) δ 8.15; 7.90; 7.70; 7.40; 7.30; 7.19; 6.82; 6.63; 6.00; 4.83; 3.30; 2.95; and 2.82. In some embodiments the compound of Formula II is characterized by $^{13}$C NMR of the peak ($^{13}$NMR, 300 MHz, DMSO-d$_6$) δ 170.0; 148.0; 145.5; 140.3; 140.1; 135.4; 133.9; 130.0; 129.6; 129.0; 128.3;

128.0; 127.3; 127.1; 125.7; 124.5; 114.8; 111.8; 110.7; 62.8; 54.8; 44.6; 40.8; 40.0; 39.8; 39.4; 39.2; 38.8; 38.6; and 25.4. In further embodiments the compound of Formula II is at least about 97.0% by weight pure. In some embodiments the compound of Formula II is at least about 98.0% by weight pure. In some embodiments the compound of Formula II is at least about 99.0% by weight pure. In further embodiments the compound of Formula II is at least about 99.5% by weigh pure. In some embodiments the compound of Formula II is at least about 99.9% by weight pure. In further embodiments the compound of Formula II has no single impurity present in an amount greater than about 0.5% by weight. In some embodiments the compound, of Formula II has no single impurity present in an amount greater than about 0.25% by weight. In further embodiments the compound of Formula II, has no single impurity present in an amount greater than about 0.10% by weight.

Figure 7:
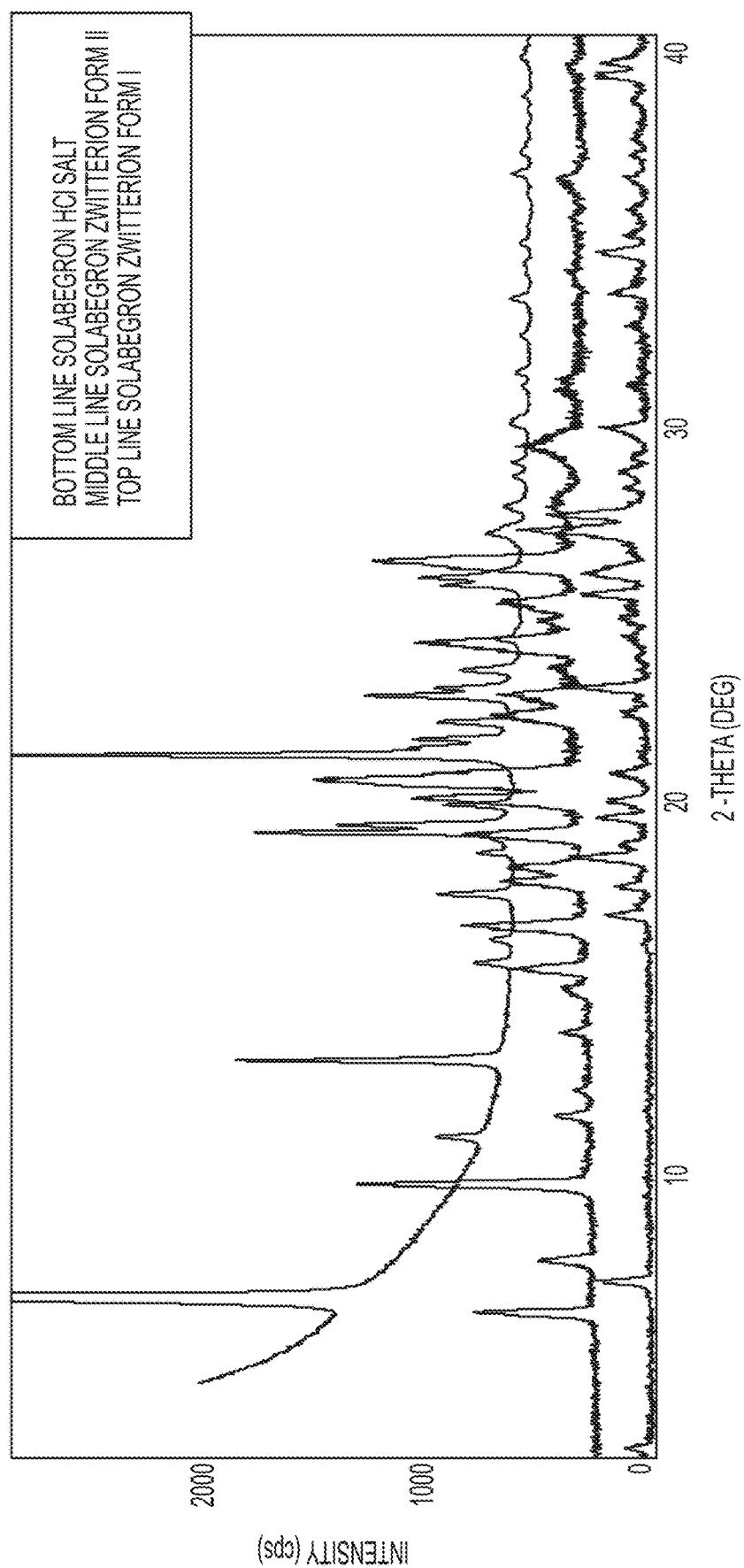
FIG. 7—is an XRPD pattern of the solabegron zwitterion Form I (top line); solabegron zwitterion Form II, (middle) and solabegron HCl salt (bottom)
Figure 12:
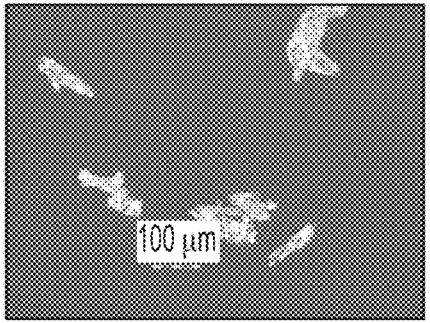
Figure 12:
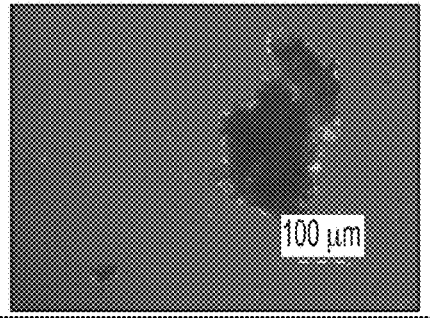
Figure 12:
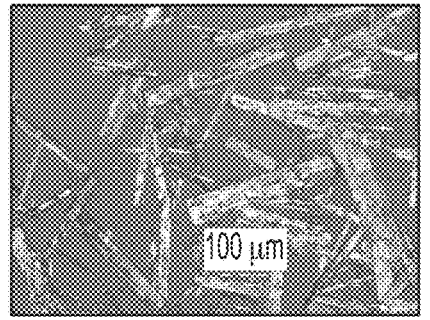
Figure 12:
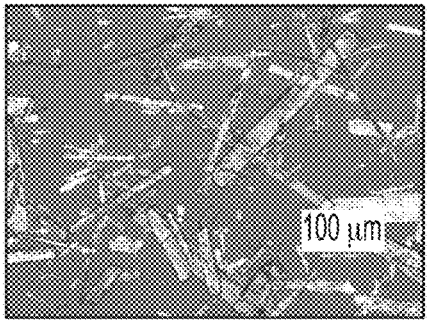

After extensive effort, applicants have newly discovered two crystalline forms of solabegron zwitterion. One form, form I, is an anhydrous crystalline form and is characterized by an x-ray powder diffraction pattern having peaks expressed in degrees 2θ (±2) at 6.2, 12.5; 18.8; 20.6; and 25.2. A second form, form II is a hydrate of isopropanol solvate and is characterized by an x-ray powder diffraction pattern having peaks expressed in degrees 2θ (±2) at 17.6, 18.7, 19.6, 20.1, 20.5, 23.7, and 25.8. (See EXAMPLE 3 and FIGS. 7, 12 and 13). Applicants also discovered that the form II solabegron zwitterion is more stable than the form I solabegron zwitterion and that the form II zwitterion crystal form (see EXAMPLE 3 and FIG. 10) afforded powerful impurity rejection and robust isolation process which is a key component for a scalable solabegron HCl process. Solabegron zwitterion as described herein is the least soluble form of solabegron, and that feature allows it to be isolated in pure form, allowing for large scale production. After isolation the solabegron crystals can be dissolved and then crystallized to the solabegron HCL salt form, which is currently being investigated clinically. Of equal importance, the pharmaceutical compositions of solabegron zwitterion disclosed herein could be used as the active ingredient clinically, replacing the need for the HCl salt form of solabegron.

Pharmaceutical Compositions of Solabegron Zwitterion (Formula II)

In one embodiment the present application describes a pharmaceutical composition comprising: a therapeutically effective amount of a compound according to Formula II:

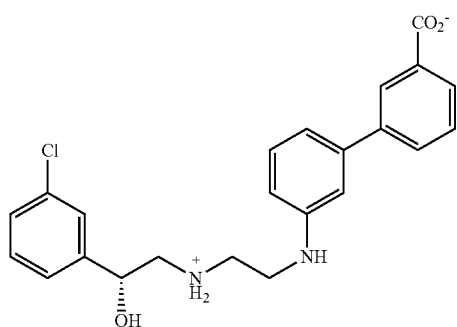

Formula II or a pharmaceutically acceptable salt, stereoisomer, solvate or polymorph; and at least one pharmaceutically acceptable carrier or excipient. In some embodiments the compound of Formula II in the composition is a solid. In some embodiments the compound of Formula II is amorphous. In further embodiments, the compound of Formula II in the composition is a crystal. In some embodiments, the compound of Formula II in the composition is a single polymorph. In further embodiments the compound of Formula II in the composition is more than one polymorph. In further embodiments, the compound of Formula II in the composition is a solid or crystalline hydrate of isopropanol solvate. In some embodiments the compound of Formula II in the composition is characterized by a peak at 1552 cm$^1$ upon infrared analysis. In further embodiments the compound of Formula II in the composition is characterized by a peak at 184.6° C. upon differential scanning calorimetry analysis. In some embodiments the compound of Formula II in the composition is characterized by an x-ray powder diffraction pattern having peaks expressed in degrees 2θ (±2) at 6.3, 12.6; 18.6; 18.9; 20.9; 22.4; 25.3; and 25.5. In some embodiments the compound of Formula II in the composition is characterized by an x-ray powder diffraction pattern having peaks expressed in degrees 2θ (±2) at 6.2, 12.5; 18.8; 20.6; and 25.2. In some embodiments the compound of Formula II in the composition is characterized by an x-ray powder diffraction pattern having peaks expressed in degrees 2θ (±2) at 6.2, 12.5; 18.6; 18.8; 20.6; 22.3, and 25.2. In some embodiments the compound of Formula II in the composition is characterized by an x-ray powder diffraction pattern having peaks expressed in degrees 2θ (±2) at 6.2, 12.5; 16.9, 18.6; 18.8; 20.6; 21.1, 21.5; 22.3, 25.2; 26.6, and 32.9. In some embodiments the compound of Formula II in the composition is characterized by an x-ray powder diffraction pattern having peaks expressed in degrees 2θ (±2) at 17.6, 18.7, 19.6, 20.1, 20.5, 23.7, and 25.8. In some embodiments the compound of Formula II in the composition is characterized by an x-ray powder diffraction pattern having peaks expressed in degrees 2θ (±2) at 9.4, 15.1, 16.2, 17.6, 18.7, 19.6, 20.1, 20.5, 21.8, 22.6, 23.7, 24.8, 25.8, and 28.9. In some embodiments the compound of Formula II in the composition is characterized by an x-ray powder diffraction pattern having peaks expressed in degrees 2θ (±2) at 6.1, 7.5, 9.4, 11.3, 14.5, 15.1, 16.2, 17.6, 18.7, 19.6, 20.1, 20.5, 21.8, 22.6, 23.7, 24.8, 25.8, and 28.9. In further embodiments the compound of Formula II, in the composition is characterized by $^1$H NMR peaks ($^1$H NMR, 300 MHz, DMSO-d$_6$) δ 8.15; 7.90; 7.70; 7.40; 7.30; 7.19; 6.82; 6.63; 6.00; 4.83; 3.30; 2.95; and 2.82. In some embodiments the compound of Formula II in the composition is characterized by $^{13}$C NMR of the peak ($^{13}$NMR, 300 MHz, DMSO-d$_6$) δ 170.0; 148.0; 145.5; 140.3; 140.1; 135.4; 133.9; 130.0; 129.6; 129.0; 128.3; 128.0; 127.3; 127.1; 125.7; 124.5; 114.8; 111.8; 110.7; 62.8; 54.8; 44.6; 40.8; 40.0; 39.8; 39.4; 39.2; 38.8; 38.6; and 25.4. In further embodiments the compound of Formula II in the composition is at least about 97.0% by weight pure. In some embodiments the compound of Formula II in the composition is at least about 98.0% by weight pure. In some embodiments the compound of Formula II in the composition is at least about 99.0% by weight pure. In further embodiments the compound of Formula II in the composition is at least about 99.5% by weigh pure. In some embodiments the compound of Formula II in the composition is at least about 99.9% by weight pure. In further embodiments the compound of Formula II in the composition has no single impurity present in an amount greater than about 0.5% by weight. In some embodiments the compound, of Formula II in the composition has no single impurity present in an amount greater than about 0.25% by weight. In further embodiments the compound of Formula II, in the composition has no single impurity present in an amount greater than about 0.10% by weight.

In some embodiments, the composition further comprises one or more additional therapeutic agents for the treatment of LUTS and/or OAB, wherein the one or more additional therapeutic agents is selected from the group consisting of: antimuscarinic agents; alpha adrenoceptor blockers; 5-alpha reductases; and phosphdiesterases-5 inhibitors.

The pharmaceutical compositions of the present application can be administered for any of the uses described herein by any suitable means, for example, orally, such as in the form of tablets, capsules, granules or powders; sublingually; bucally; vaginally, such as via intravaginal ring; parenterally, such as by subcutaneous, intravenous, intramuscular, or intrasternal injection or infusion techniques (e.g., as sterile injectable aqueous or non-aqueous solutions or suspensions); in dosage unit formulations containing non-toxic, pharmaceutically acceptable vehicles or diluents. The present compositions can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compositions can also be administered liposomally.

The pharmaceutical composition of the present invention can formulated for a pulsatile drug-delivery system wherein the composition releases at least two pulses of the compound according to Formula II, wherein a first pulse achieves a first target $C_{max}$, a second pulse achieves a second target $C_{max}$, a first target $C_{min}$ is achieved between the first pulse and the second pulse and a second $C_{min}$ is achieved after the second pulse.

The formulation for a beta 3 adrenoceptor agonist can significantly modify the absorption profile. For example, some compounds are differentially absorbed in different regions of the GI tract. Some of the factors involved in absorption can include pH-dependent solubility, particle size, lipophilicity, ionization, GI-motility or transporters. Accordingly, the solabegron zwitterion and pharmaceutical salts thereof display the optimum absorption in the proximal GI tract. Pharmaceutical compositions are presented herein that improve the pH-dependent solubility of the solabegron zwitterion in the distal GI tract. Under these improved conditions, a second pulse of the solabegron zwitterion release and absorption will result. Additionally, methods for the release of the solabegron zwitterion in the distal GI tract based on pH are presented herein.

Another example of producing a delayed second pulse is based on the transit time of the dosage form. This is achievable through the time-dependent erosion of the dosage form coating. The GI transit time is well understood, and the coatings are designed to erode within a specific time range that corresponds to a specific region within the GI tract. Pharmaceutical compositions and methods of use are presented herein for the release of the dosage form on time-dependent erosion.

Exemplary compositions for oral administration include emulsions and suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compositions of the present application can also be delivered through the oral cavity by sublingual and/or buccal administration. Molded tablets, compressed tablets or freeze-dried tablets are exemplary forms which may be used. Exemplary compositions include those formulating the present beta-3 adrenoceptor agonists with fast dissolving diluents such as mannitol, lactose, sucrose and/or cyclodextrins. The compositions of the present application may take the form of pulsatile delivery systems such as, for example, PULSINCAP®, MICROPUMP®, MEDUSA™, PORT® system, CHRONOTROPIC®, TIME CLOCK®, multilayered tablets, DiffuCORE®, rupturable tablets, ACCU-BREAK® system, DIFFUCAPS®, DIFFUTABS®, Eurand MINITABS®, MICROCAPS®, SODAS®, IPDAS®, OsDrC®, OptiDose™, OptiMelt™, ZYDIS®, CODAS®, PRODAS®, TMDS®, DMDS®, PMDS®, GEOCLOCK®, GEOMATRIX®, PULSYS®, OROS® INTELLIMATRIX™ and VERSETROL™. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

The therapeutic agents in the pharmaceutical compositions of the present application may exist in any physical form known to one of skill in the art such as, for example, nanoparticles, crystalline solids, amorphous solids, polymorphs, pharmaceutically acceptable salts, hydrates, solvates, stereoisomers, solutions and suspensions. Crystalline solids have regular ordered arrays of components held together by uniform intermolecular forces, whereas the components of amorphous solids are not arranged in regular arrays. Hydrates are substances that incorporate water molecules into their crystalline matrix. Solvates are substances that incorporate solvent molecules into their crystalline matrix. Polymorphs exhibit different crystalline structures for molecules that have the same molecular formula and sequence of bonded atoms. Stereoisomers are isomeric molecules that have the same molecular formula and sequence of bonded atoms (constitution), but that differ only in the three-dimensional orientations of their atoms in space.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for transdermal administration include transdermal therapeutic systems (hereinafter "TTS"). TTS are patches having a layered structure and comprising at least one active pharmaceutical ingredient in a reservoir layer. A distinction is made between matrix-type and reservoir-type TTS: in the first case the reservoir layer containing the active pharmaceutical ingredient has a pressure-sensitive adhesive finish, and in the second case a membrane which controls the rate of release of the active pharmaceutical ingredient, and where appropriate an additional pressure-sensitive adhesive layer, are present.

It will be understood that the specific dose level and frequency of dosage for any particular subject can be varied and will depend upon a variety of factors including the activity of the specific beta-3 adrenoceptor agonist employed, the metabolic stability and length of action of that compound, the species, age, body weight, general health, sex and diet of the subject, the mode and time of administration, rate of excretion, drug combination, and severity of the particular condition.

Method of Treating LUTS and/or OAB

In one embodiment the present application describes a method for treating LUTS, comprising: administering a therapeutically effective amount of a compound according to Formula II or a pharmaceutically acceptable salt, stereoisomer, solvate or polymorph to a patient in need thereof. Further embodiments of the application describe the method, wherein the LUTS is overactive bladder. Further embodiments of the application describe the method, wherein the LUTS is prostate disorder. Further embodiments of the application describe the method, wherein the LUTS exhibits symptoms selected from the group consisting of: frequency of urinary urgency; nocturia; increase in urinary micturition frequency; and urinary incontinence.

In one embodiment the present application describes a method for treating LUTS, comprising: administering a therapeutically effective amount of a pharmaceutical composition comprising a therapeutically effective amount of a compound according to Formula II or a pharmaceutically acceptable salt, stereoisomer, solvate or polymorph and a pharmaceutically acceptable carrier or diluent to a patient in need thereof. Further embodiments of the application describe the method, wherein the LUTS is overactive bladder. Further embodiments of the application describe the method, wherein the LUTS is prostate disorder. Further embodiments of the application describe the method, wherein the LUTS exhibits symptoms selected from the group consisting of: frequency of urinary urgency; nocturia; increase in urinary micturition frequency; urinary incontinence and reduction in voided volume.

Therapeutically effective amounts of the compound according to Formula II:

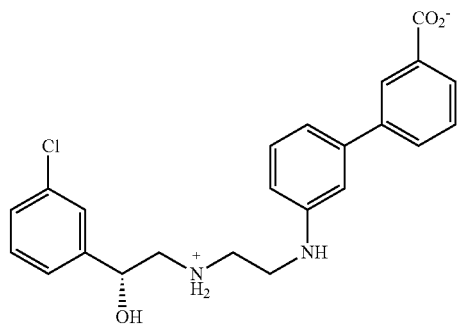

or a pharmaceutically acceptable salt or a stereoisomer or a solvate or a polymorph thereof may be from about 50 mg to about 1 gm, from about 100 mg to about 600 mg, from about 100 mg to about 500 mg, from about 100 mg to about 300 mg, from about 100 mg to 200 mg, from about 150 mg to about 300 mg, from about 150 mg to about 200 mg, from about 175 mg to about 300 mg, about 50 mg, about 100 mg, about 150 mg, about 175 mg, about 200 mg, about 225 mg, about 250 mg, about 275 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 and about 1 gm. This therapeutically effective amount may be administered once a day, twice a day or three times a day.

In some embodiments the total daily dose is from 175 mg to 300 mg. In some embodiments the total daily dose is 175 mg, 200 mg, 225 mg, 250 mg, 275 mg, Or 300 mg.

In some embodiments, the method further comprises administering one or more additional therapeutic agents for the treatment of LUTS and/or OAB, wherein the one or more additional therapeutic agents is selected from the group consisting of: antimuscarinic agents; alpha adrenoceptor blockers; 5-alpha reductases; and phosphdiesterases-5 inhibitors.

Pharmaceutical Combinations

The present application also includes within its scope pharmaceutical compositions comprising, as an active ingredient, a therapeutically effective amount of the solabegron zwitterion, alone or in combination with a pharmaceutical carrier or diluent. Optionally, the pharmaceutical compositions of the present invention can be used alone, or in combination with other suitable therapeutic agents useful in the treatment of the LUTS including: antimuscarinic agents, alpha adrenoceptor blockers, 5-alpha reductases and phosphodiesterase-5 inhibitors.

Such other therapeutic agent(s) may be administered prior to, simultaneously with, or following the administration of the beta-3 adrenoceptor agonist containing pharmaceutical composition in accordance with the invention.

Examples of suitable antimuscarinic agents for use in combination with the pharmaceutical compositions of the present application include tolterodine, oxybutynin, trospium, solifenacin, darifenacin, propiverine, fesoterodine, and pharmaceutically acceptable salts thereof.

Examples of suitable alpha adrenoceptor blockers for use in combination with the pharmaceutical compositions of the present application include tamuslosin, alfuzosin, and silodosin.

Examples of suitable 5-alpha reductases for use in combination with the pharmaceutical compositions of the present application include finasteride, dutasteride and pharmaceutically acceptable salts thereof.

Examples of suitable phosphodiesterase-5 inhibitors for use in combination with the pharmaceutical compositions of the present application include sildenafil, tadalafil, vardenafil, udenafil, avanafil and pharmaceutically acceptable salts thereof.

Synthesis

Solabegron (Formula I), solabegron hydrochloride salt, (Formula I-HCl), the solabegron zwitterion (Formula II) or a another pharmaceutically acceptable salt or a stereoisomer or a solvate or a polymorph thereof may be prepared by the following synthetic routes as illustrated below.

A mixture of (3-nitrophenyl)boronic acid and methyl 3-bromobenzoate was placed into a reaction vessel with 10% palladium on carbon (Pd/C) and sodium carbonate (Na2CO₃) in methanol (MeOH). The reaction mixture was held at reflux until the starting materials had been converted into methyl 3'-nitro-[1,1'-biphenyl]-3-carboxylate. The methyl 3'-nitro-[1,1'-biphenyl]-3-carboxylate was maintained in the reaction vessel, used without purification, isopropyl acetate was added to the reaction vessel and the mixture subsequently reacted with 10% Pd/C in a hydrogen atmosphere to yield methyl 3'-amino-[1,1'-biphenyl]-3-carboxylate according to Formula V. N-(2-chloroethyl)acetamide was reacted with 2.5 equivalents of phosphoryl chloride (POCl$_3$) in ethyl acetate (EtOAc) on warming from 0 to 25° C. to yield (Z)—N-(2-chloroethyl)acetimidoyl chloride dichlorophosphate according to Formula VI that was added without purification to methyl 3'-nitro-[1,1'-biphenyl]-3-carboxylate according to Formula V to yield methyl (E)-3'-N-(2-chloroethyl)acetimiamido-[1,1'-biphenyl]-3-carboxylate hydrochloride according to Formula VII that was used without purification. To the reaction vessel was added 5.33 equivalents of NH$_3$ as a saturated aqueous solution (approximately 35% NH$_3$ by mass). The resulting reaction mixture yielded methyl 3'-(2'methyl-4,5-dihydro-1H-imidazol-1-yl)-[1,1']biphenyl-3-carboxylate according to Formula IV.

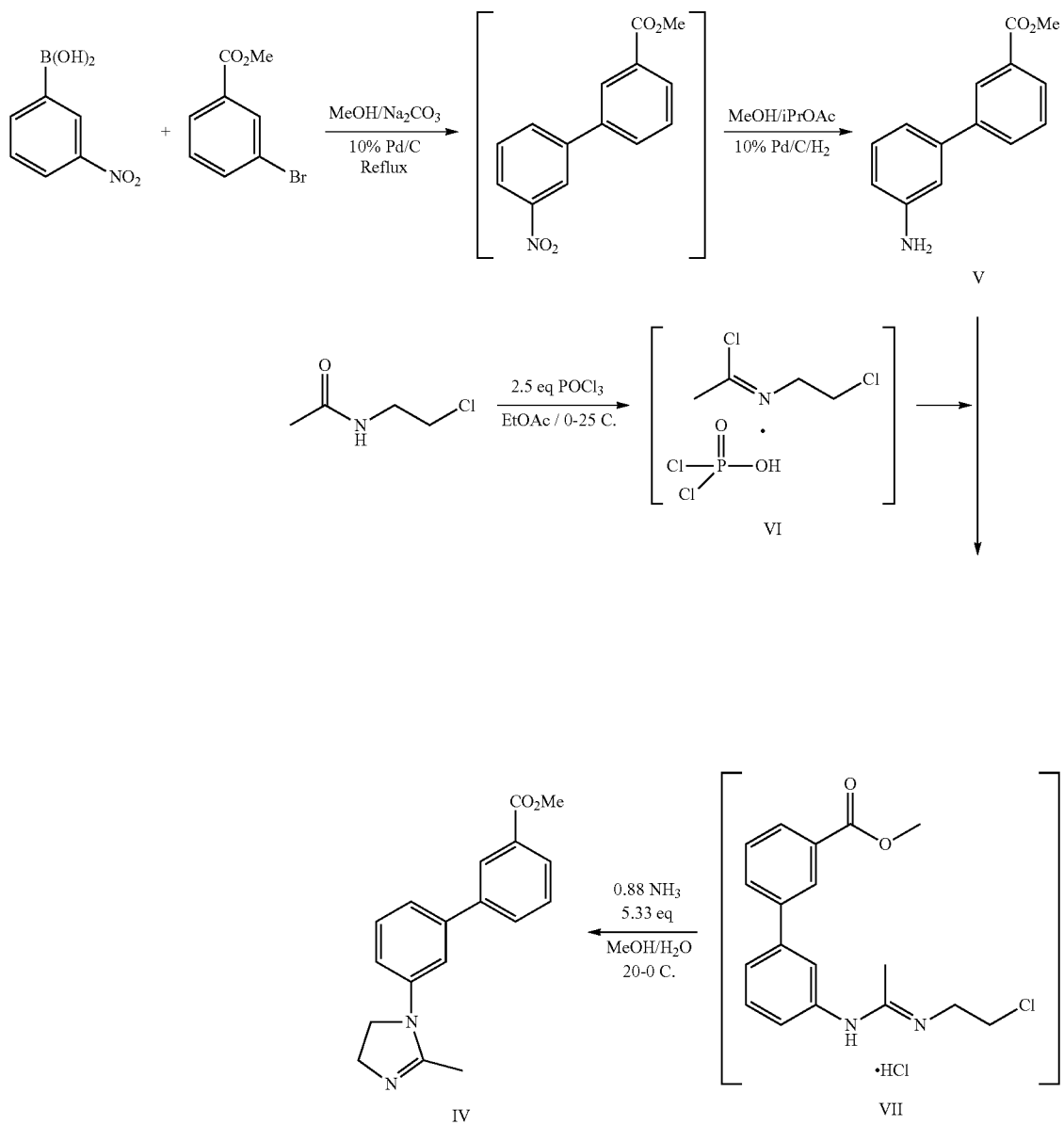

The coupling of the imidazoline ring on the compound according to Formula IV with the epoxide ring of (R)-2-(3-chlorophenyl)oxirane yields methyl 3'-((2R)-2-(3-chlorophenyl)-7a-methyltetrahydroimidazol[2,1,b]oxazole-7 (7aH)-yl)-[1,1'-biphenyl]-3-carboxylate according to Formula III that opens upon treatment with from about 1 to about 5 equivalents sodium hydroxide (about 5% to about 50% w/w) to yield the solabegron sodium salt according to Formula I-Na.

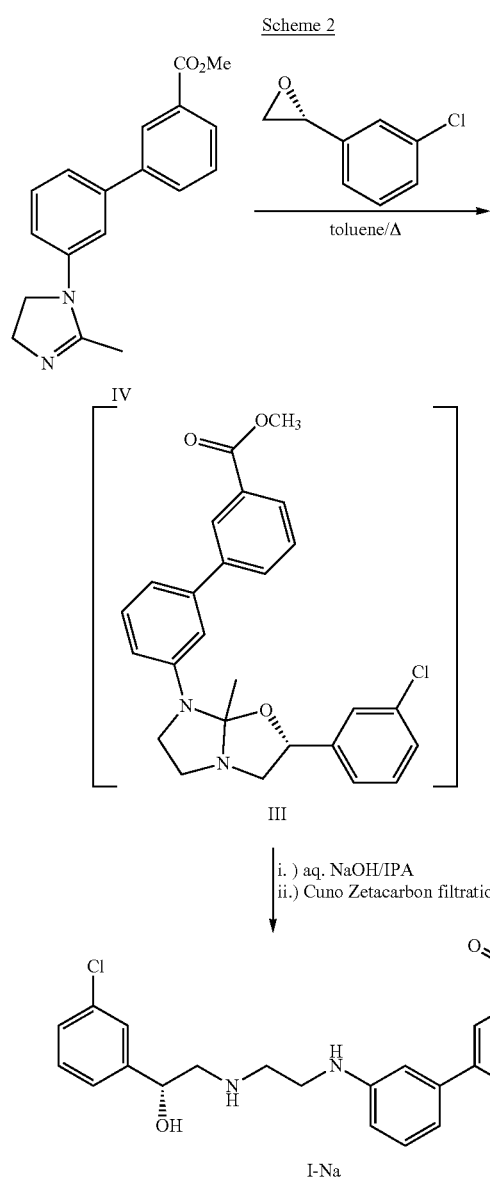

The recovered solabegron sodium salt according to Formula I-Na was utilized without purification. The addition of about 25% w/w NaOH solution yielded a slurry that was slowly neutralized at 55° C. with about 0.9 equivalents of 1N HCl. After approximately 50% of the HCl had been added 2% by weight of the solabegron zwitterion according to Formula II was added to the reaction mixture to induce crystallization of the solabegron zwitterion according to Formula II. The solabegron zwitterion was collected, dried and checked for purity before being converted into the solabegron hydrochloride salt according to Formula I-HCl by the slow addition of 1.0 equivalent of 1N HCl to a slurry of the solabegron zwitterion in water as illustrated in Scheme 3.

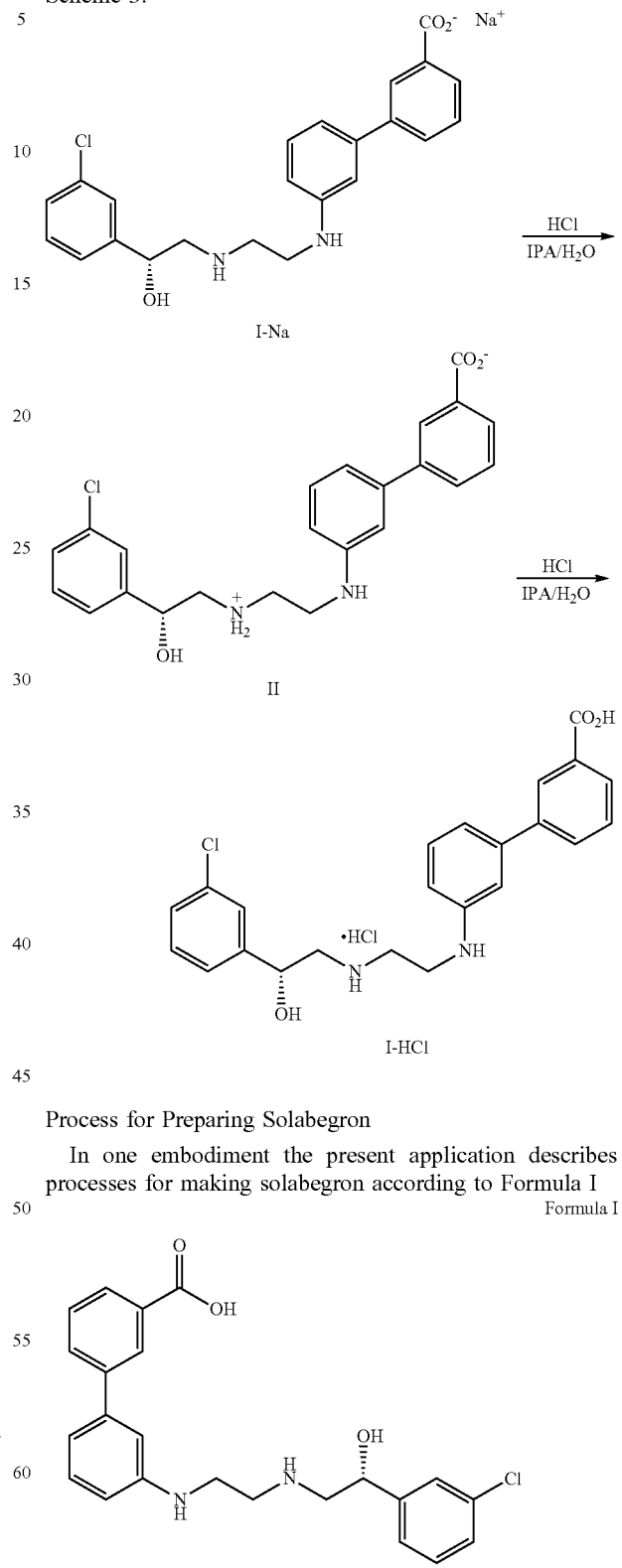

Process for Preparing Solabegron

In one embodiment the present application describes processes for making solabegron according to Formula I Formula I comprising contacting the imidazo[2,1,b]oxazole intermediate according to Formula III

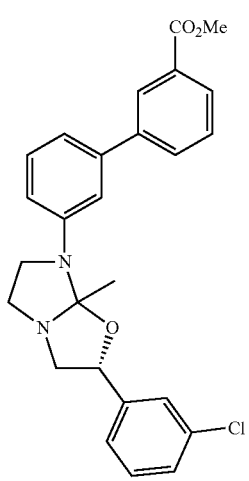

Formula III with aqueous sodium hydroxide (NaOH) in a reaction vessel.

In one embodiment the present application describes processes for making solabegron hydrochloride salt according to Formula I-HCl

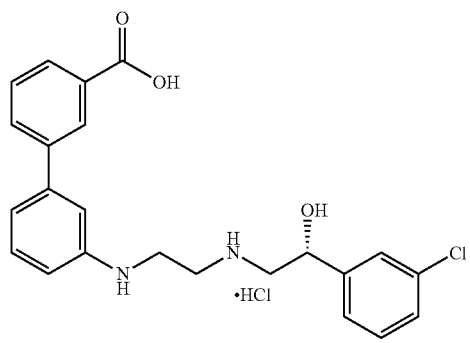

Formula I comprising: contacting the imidazo[2,1,b]oxazole intermediate according to Formula III

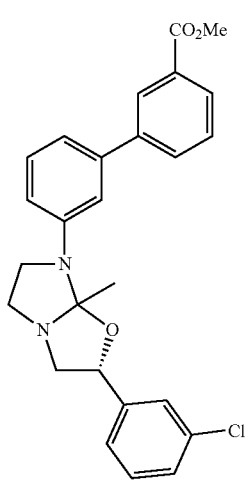

Formula III with aqueous sodium hydroxide (NaOH) in a reaction vessel. Further embodiments describe processes, wherein the NaOH is present from about 1 equivalent to about 5 equivalents. Further embodiments describe processes, wherein the reaction vessel additionally contains isopropyl alcohol. Further embodiments describe processes, wherein solabegron hydrochloride salt is formed by the addition of hydrochloric acid (HCl) to the reaction vessel.

In one embodiment the present application describes processes for making the hydrochloride salt of solabegron according to Formula I-HCl

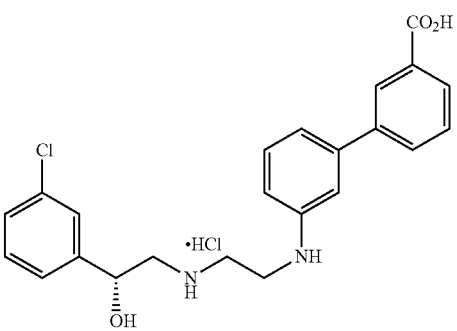

Formula I-HCl comprising contacting a zwitterion of Formula II

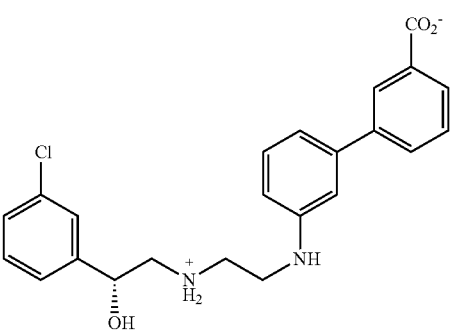

Formula II with hydrochloric acid in a reaction vessel. Further embodiments describe processes wherein the HCl is 6N HCl. Further embodiments describe processes wherein the HCl to zwitterion ratio is 1.2 equivalents. Further embodiments describe processes that include seeding the reaction mixture to induce crystallization. Further embodiments describe processes wherein the reaction temperature is 50-62° C. Further embodiments describe processes wherein the solvent is IPA H$_2$O. Further embodiments describe processes wherein the seed load is 05-5%. Further embodiments describe processes wherein the seeding point pH is 6.6-7.2.

In one embodiment the present application describes processes for making, zwitterion of Formula II,

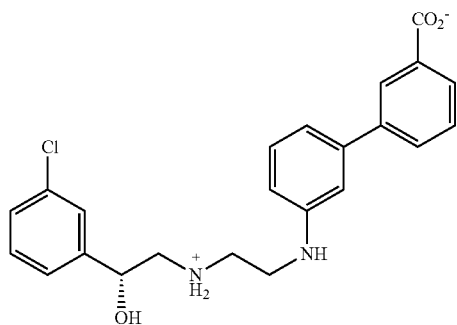

Formula II comprising contacting a sodium salt according to Formula I-Na

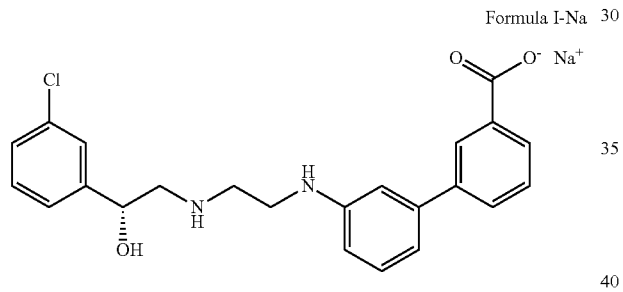

Formula I-Na with hydrochloric acid.

In one embodiment the present application describes processes for making the sodium salt according to Formula I-Na

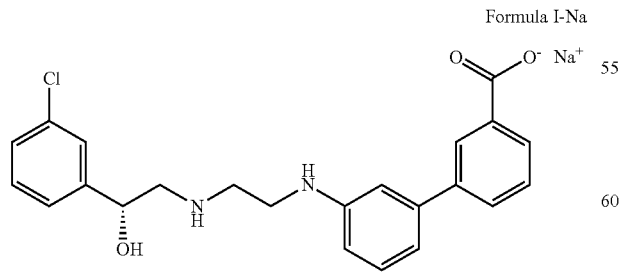

Formula I-Na comprising contacting an imidazo[2,1,b]oxazole intermediate according to Formula III

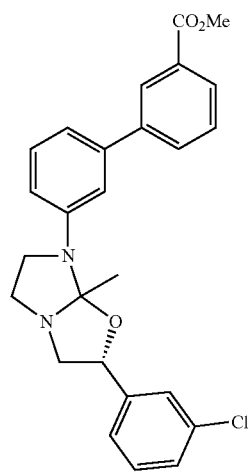

Formula III with aqueous sodium hydroxide (NaOH) in a reaction vessel. Further embodiments describe processes, wherein the NaOH is present from about 1 equivalent to about 5 equivalents. Further embodiments describe processes, wherein the reaction vessel additionally contains isopropyl alcohol.

In one embodiment the present application describes processes for making imidazo[2,1,b]oxazole intermediate according to Formula III Formula III comprising contacting methyl 3'-(2'methyl-4,5-dihydro-1H-imidazol-1-yl)-[1,1']biphenyl-3-carboxylate according to Formula IV

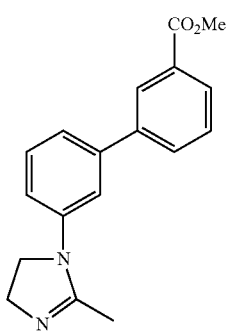

Formula IV with (R)-2-(3-chlorophenyl)oxirane.

In one embodiment the present application describes processes for making methyl 3'-(2'methyl-4,5-dihydro-1H-imidazol-1-yl)-[1,1']biphenyl-3-carboxylate according to Formula IV or a pharmaceutically acceptable salt or a stereoisomer or a solvate or a polymorph thereof

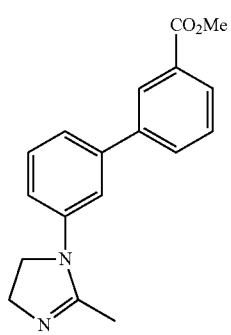

Formula IV comprising contacting the biphenyl amine according to Formula V

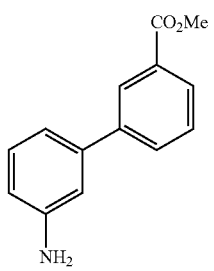

Formula V with the acetimidoyl chloride according to Formula VI

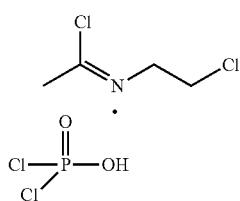

Formula VI wherein the acetimidoyl chloride is generated in situ from the reaction of N-(2-chloroethyl)acetamide and phosphoryl chloride. Further embodiments describe processes, wherein the phosphoryl chloride is present from about 1 equivalent to about 5 equivalents. Further embodiments describe processes, wherein the phosphoryl chloride is dissolved in ethyl acetate (EtOAc). Further embodiments describe processes, wherein the biphenyl aniline according to Formula V and the acetimidoyl chloride according to Formula VI react to form the acetimiamido biphenyl according to Formula VII

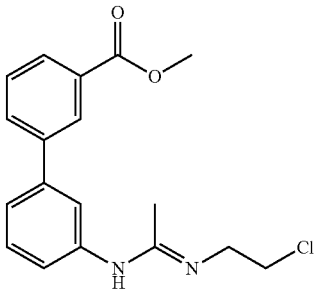

Formula VII or a pharmaceutically acceptable salt or a stereoisomer or a solvate or a polymorph thereof.

In one embodiment the present application describes processes for making the biphenyl amine according to Formula V

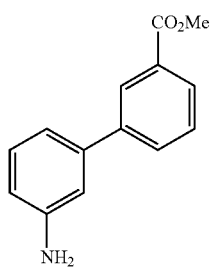

Formula V comprising coupling (3-nitrophenyl)boronic acid and methyl 3-bromobenzoate In one embodiment the present application describes processes for making the solabegron sodium salt according to Formula I-Na

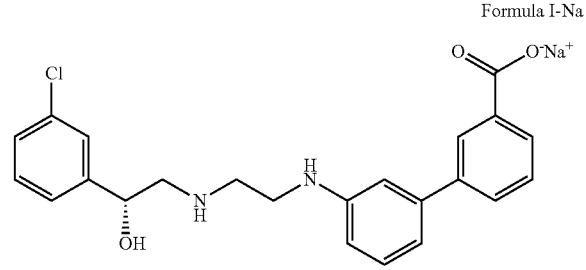

Formula I-Na comprising: contacting the imidazo[2,1,b]oxazole intermediate according to Formula III

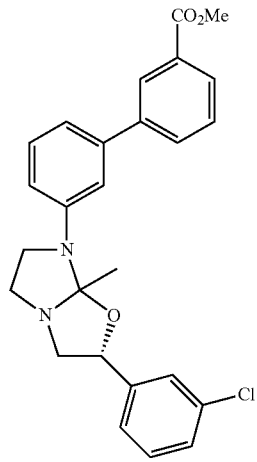

Formula III with aqueous sodium hydroxide (NaOH)

In one embodiment the present application describes a compound according to Formula III or a pharmaceutically acceptable salt or a stereoisomer or a solvate or a polymorph thereof.

In one embodiment the present application describes a compound according to Formula IV or a pharmaceutically acceptable salt or a stereoisomer or a solvate or a polymorph thereof.

EXAMPLES

Example 1: Preparation of methyl 3'-(2'methl-4,5-dihydro-1H-imidazol-1-yl)-[1,1']biphenyl-3-carboxylate (Formula IV)

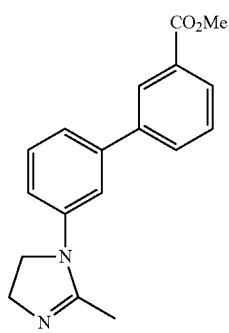

Formula IV

A mixture of (3-nitrophenyl)boronic acid and methyl 3-bromobenzoate was placed into a reaction vessel with 10% palladium on carbon (Pd/C) and sodium carbonate (Na$_2$CO$_3$) in methanol (MeOH). The reaction mixture was held at reflux until the starting materials had been converted into methyl 3'-nitro-[1,1'-biphenyl]-3-carboxylate. The methyl 3'-nitro-[1,1'-biphenyl]-3-carboxylate was maintained in the reaction vessel, used without purification, isopropyl acetate was added to the reaction vessel and the mixture subsequently reacted with 10% Pd/C in a hydrogen atmosphere to yield methyl 3'-amino-[1,1'-biphenyl]-3-carboxylate.

Concurrently, N-(2-chloroethyl)acetamide was reacted 2.5 equivalents of phosphoryl chloride (POCl$_3$) in ethyl acetate (EtOAc) on warming from 0 to 25° C. to yield (Z)—N-(2-chloroethyl)acetimidoyl chloride dichlorophosphate.

The (Z)—N-(2-chloroethyl)acetimidoyl chloride dichlorophosphate was added without purification to methyl 3'-nitro-[1,1'-biphenyl]-3-carboxylate to yield methyl (E)-3'-N-(2-chloroethyl)acetimiamido-[1,1'-biphenyl]-3-carboxylate hydrochloride that was used without purification. To the reaction vessel was added 5.33 equivalents of NH$_3$ as a saturated aqueous solution (approximately 35% NH$_3$ by mass). The resulting reaction mixture yielded the desired methyl 3'-(2'methl-4,5-dihydro-1H-imidazol-1-yl)-[1,1']biphenyl-3-carboxylate (Formula IV).

Example 2: Preparation of Solabegron Sodium Salt (Compound of Formula I-Na)

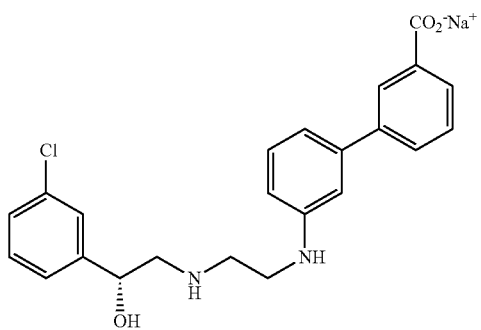

Formula I-Na

Step 1: Preparation of Intermediate Formula III via alkylation of methyl 3'-(2'methyl-4,5-dihydro-1H-imidazol-1-yl)-[1,1']biphenyl-3-carboxylate (Formula IV)

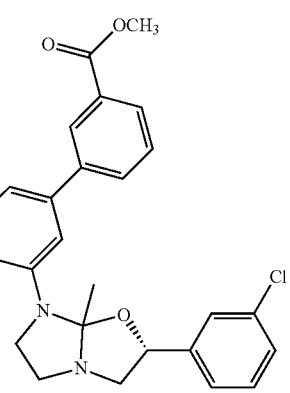

Formula III

Methyl 3'-(2'methl-4,5-dihydro-1H-imidazol-1-yl)-[1,1'] biphenyl-3-carboxylate (Formula IV, 205.2 g, 96.6 wt %, 67.4 mmol, 1.0 eq) and toluene (1 L, 5 Vol) were added to a 2-L round bottom flask, and the resulting slurry was heated to 55-60° C. in a heating bath to dissolve. The resulting solution was concentrated on a rotary evaporator under partial vacuum (80-115 mbar) at bath temperature of 50-55° C. to ~⅓ of the original volume. Toluene (1 L, 5 Vol) was added to the reaction mixture and the resulting solution was concentrated a second time on a rotary evaporator under partial vacuum (80-115 mbar) at bath temperature of 50-55° C. to ~⅓ of the original volume. Toluene (1 L, 5 Vol) was added to the reaction mixture and the resulting solution was concentrated a third time on a rotary evaporator under partial vacuum (80-115 mbar) at bath temperature of 50-55° C. to ~⅓ of the original volume. The KF was checked and found to be within an acceptable range (KF=49 ppm, 24.3 μg/0.5 mL) so the reaction mixture was allowed to continue to concentrate on the rotary evaporator to ~300 mL. The concentrates were transferred to a 1-L jacketed vessel and rinsed with toluene and the batch volume was 400 mL. The toluene mixture was then heated to 60° C., add (R)-3-chlorostyrene oxide (100.0 g, 647 mmol, 0.96 eq) was added in one portion. The reaction mixture was heated to 120° C. over 15-30 min and maintained at 120° C. for 20-22 h. The reaction mixture (orange solution) was sampled by taking about 5 μL liquid into a LC vial, diluting with MeCN to ~1.2 mL for HPLC analysis. The conversion was found to be 94.3 A % (spec≥96 A %, the ratio of LC area percent of Compound of Formula III to the combined area % of methyl 3'-(2'methl-4,5-dihydro-1H-imidazol-1-yl)-[1,1' ]biphenyl-3-carboxylate (Compound of Formula IV) and Compound of Formula III). Therefore the reaction was stopped by cooling to 45-50° C.

Step 2: Conversion of Intermediate Formula III to Solabegron-Na (Compound of Formula I-Na)

After completion of the alkylation reaction, the crude Intermediate Formula III reaction mixture of Step 1, was transferred to a 3 L round bottom flask with a heating mantle and magnetic stirrer. The solution was heated to 60-70° C., and IPA (900 mL) was added while maintaining the same temperature. 25% w/w NaOH aqueous solution (323.5 g, ~249 mL) and water (840 mL) were added to the reaction mixture slowly, while maintain the temperature at 60-70° C. The toluene was remove from the reaction mixture by atmospheric distillation. The initial temperature is 78° C. when the distillation starts. When a total of ~1 L distillate is collected (temperature is 81-83° C.), the distillation is ended by adding IPA (620 mL). The mixture was then heated to 81-83° C. under gentle reflux and kept at the same temperature for 15 h. A 5 L sample of the reaction mixture was removed, the sample was diluted with 30:70 v/v MeCN/H$_2$O to ~1.2 mL and analyzed by HPLC analysis which indicated that the Intermediate Formula II was fully converted to the solabegron sodium salt (Compound of Formula I-Na). The reaction mixture was cooled to 40° C. Activated Carbon, Decolorizing (58 g) was added to the batch solution in one portion at 40° C. The resulting black mixture was stirred at 40° C. for 2 h. The mixture was then filtered (Solka Floc® (80 g) was added to a 2 L sintered glass funnel and pre-washed with 1:1 v/v IPA/water 2×300 mL. Used solvents were discarded by filtration) to remove used solid charcoal and the black cake was washed with 1:1 v/v IPA/water 1×200 mL. The combined filtrate was passed through a 0.45 micron PTFE in-line filter as a polish filtration, giving solabegron-Na stock solution (2195 g, 10.5 wt %) in 83% overall yield from methyl 3'-(2'methl-4,5-dihydro-1H-imidazol-1-yl)-[1,1']biphenyl-3-carboxylate (Formula IV).

Example 3: Preparation of the Solabegron Zwitterion (Formula II) from Solabegron-Na (Compound of Formula I-Na)

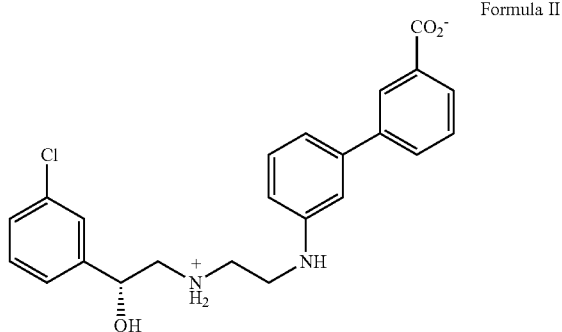

Figures 1, 6:
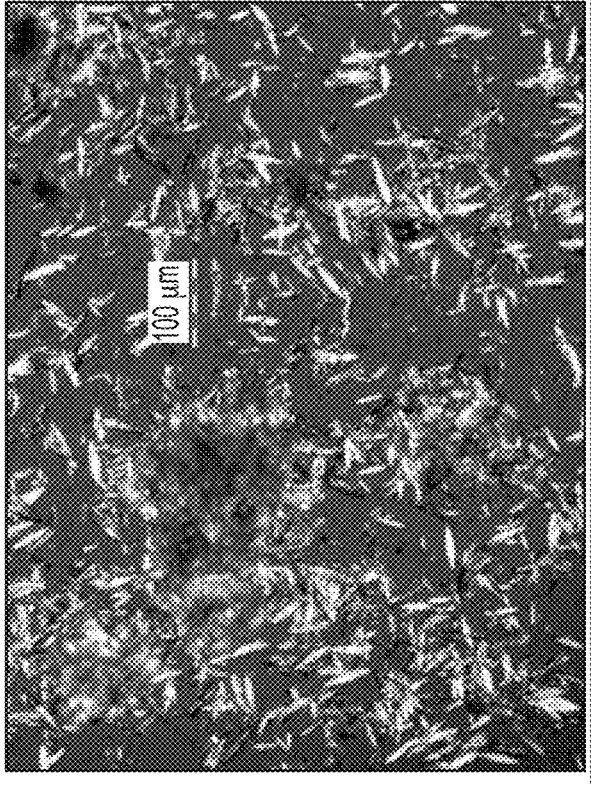

Solabegron Zwitterion Form I 37.1 mL of solabegron sodium salt (equivalent to 5.91 g of HCl salt, 13.2 mmol) was added to an EasyMax 100 mL vessel, IPA/water=~20:80 v/v. Agitation was set at 400 rpm and the reaction mixture was heated to 55° C. 1N HCl was added via syringe pump at rate of 3.3 mL/h at 55° C. After 12.5 mL 1N HCl was added, the batch turned hazy. Solabegron zwitterion seed (596-106, 59 mg) was added in one portion. Solabegron zwitterion seed did not survive. After a total of 15 mL 1N HCl was added, a 2nd portion of solabegron seed (596-106, 59 mg) was added. Solabegron seed did not survive again. After a total of 17 mL 1N HCl was added, a 3rd portion of solabegron zwitterion seed (596-106, 59 mg) was added. Solabegron zwitterion seed did survive this time. A total of 25 mL 1N HCl (1.89 eq) was added to reach a pH 7.8 (vs. 9.5 with purified solabegron). The mixture was aged at 55° C. for 1 h, cooled to 25° C. over 3 h, then at RT for the overnight. Slurry was isolated by filtration, the wet cake was washed with 1:9 v/v IPA/water 1×30 mL, followed by water 2×30 mL. After drying at ambient temperature under vacuum for 5 h, the partially dried solabegron zwitterion as beige solid (4.55 g after subtracting seed) was analyzed by LC assay giving 95.6 A % (87.6 wt %) in 83.8% isolated yield (corrected with wt %). FIG. 6

Solabegron Zwitterion Form II

Procedure A: HCl in Water Procedure

Solabegron-Na stock solution (50.0 g, 10 wt % in 1:1 v/v IPA/water, equiv to 5.0 g of solabegron zwitterion, 12.17 mmol) was charged into EasyMax 100 mL vessel with temperature probe, pH probe (pre-calibrated at pH 4.00, 7.00, and 10.00), condenser and nitrogen bubbler. The ignition agitation rate was set to 450 rpm. The reaction mixture was heated to 55° C. over 30 min. The reaction mixture had a pH of 13.3. 1N HCl was added in water at the rate of 7.5 mL/h via a syringe pump, keeping the reaction at 55° C. When a total of 8 mL 1N HCl was added (pH=10.1), a ~0.5 mL aliquot solution was removed to a 4 mL size vial and ~2 mg solabegron-zwitterion seed was added. All of the seed dissolved. The above procedure to find a proper seeding point, was repeated at pH=9.4, 8.8, 8.2, 7.8 and 7.6. Seeds were not survived under all of these conditions.

When the reaction mixture reached a pH of 7.5 (total 13 mL 1N HCl added), 50 mg of solabegron-zwitterion seed (Form I) was added and the batch turned hazy. The slurry was checked by PLM which showed a new type of crystal (by morphology). After a total 20 mL of 1N HCl was added the reaction mixture was at a pH of 6.9. the addition of HCl was stopped. The reaction mixture was aged at 55° C. for 3.5 h, cooled to 20° C. over 5 h, then aged at 20° C. for 16 h. An additional 0.2 mL of 1N HCl was added over 5 min at 20° C. to adjust the reaction mixture pH from 8.0 to 7.1. The reaction mixture was aged at 20° C. for 1 h. The sample for PLM, remained as a new crystal morphology. The solids were isolated by filtration and the filter cake was washed with 20:80 v/v IPA/water 1×20 mL, followed by water 2×20 mL. The solid was dried at ambient temperature under vacuum for 3 h, followed by drying in a vacuum oven at 50° C. for 20 h. 5.0 g off-white dry solid was obtained and a sample of the solid was analyzed by XRPD for crystal form (giving a distinct new XRPD pattern, FIGS. 7, and 14), and PLM for crystal morphology (distinctively different from zwitterion Form I, FIG. 6). The solid contains 2.8 wt % of water by KF, 2.1 wt % of IPA by GC.

Procedure B: HCl in IPA Procedure

Solabegron-Na stock solution (50.0 g, 10 wt % in 1:1 v/v IPA/water, equiv to 5.0 g of solabegron zwitterion, 12.17 mmol) was charged into an EasyMax 100 mL vessel with temperature probe, pH probe (pre-calibrated at pH 4.00, 7.00, and 10.00), condenser and nitrogen bubbler. The agitation rate was set to 450 rpm, the reaction mixture was heated to 55° C. over 30 min. The reaction pH was 13.2. 1-1.2N HCl in IPA was added at a rate of 7.5 mL/h via a syringe pump at 55° C. HCl addition was stopped when pH 7.1 was reached (total 13 mL HCl added), no oiled out was observed. A crystalline zwitterion seed (the dry solids from Procedure A, solabegron zwitterion Form II, 2%, 100 mg) was added in one portion, and seed beds formed instantly. The slurry was aged at 55° C. for 3 h. The reaction mixture was cooled to 20° C. over 5 h. Then aged at 20° C. for 5-20 h. The pH of the reaction mixture was adjusted to pH 7.2 from 8.0 by adding 1-1.2N HCl in IPA (5 mL) over 20 min. The slurry was aged at 20° C. for 2-5 h. The solids were isolated by filtration and the filter cake was washed with 20:80 v/v IPA/water 1×20 mL, followed by water 2×20 mL. The solids were dried at ambient temperature under vacuum for 3 h, followed by drying in a vacuum oven at 50° C. for 20 h. 4.42 g off-white dry solids was obtained. The solid sample was analyzed by XRPD for crystal form, and PLM for crystal morphology (FIG. 6).

Crystal form of solabegron zwitterion (designated as Form II) was generated from Procedure A, seeded with solabegron zwitterion Form I. Procedure B was seeded with solabegron zwitterion Form II (the zwitterion product from Procedure A) and produced solabegron zwitterion Form II.

Figure 8:
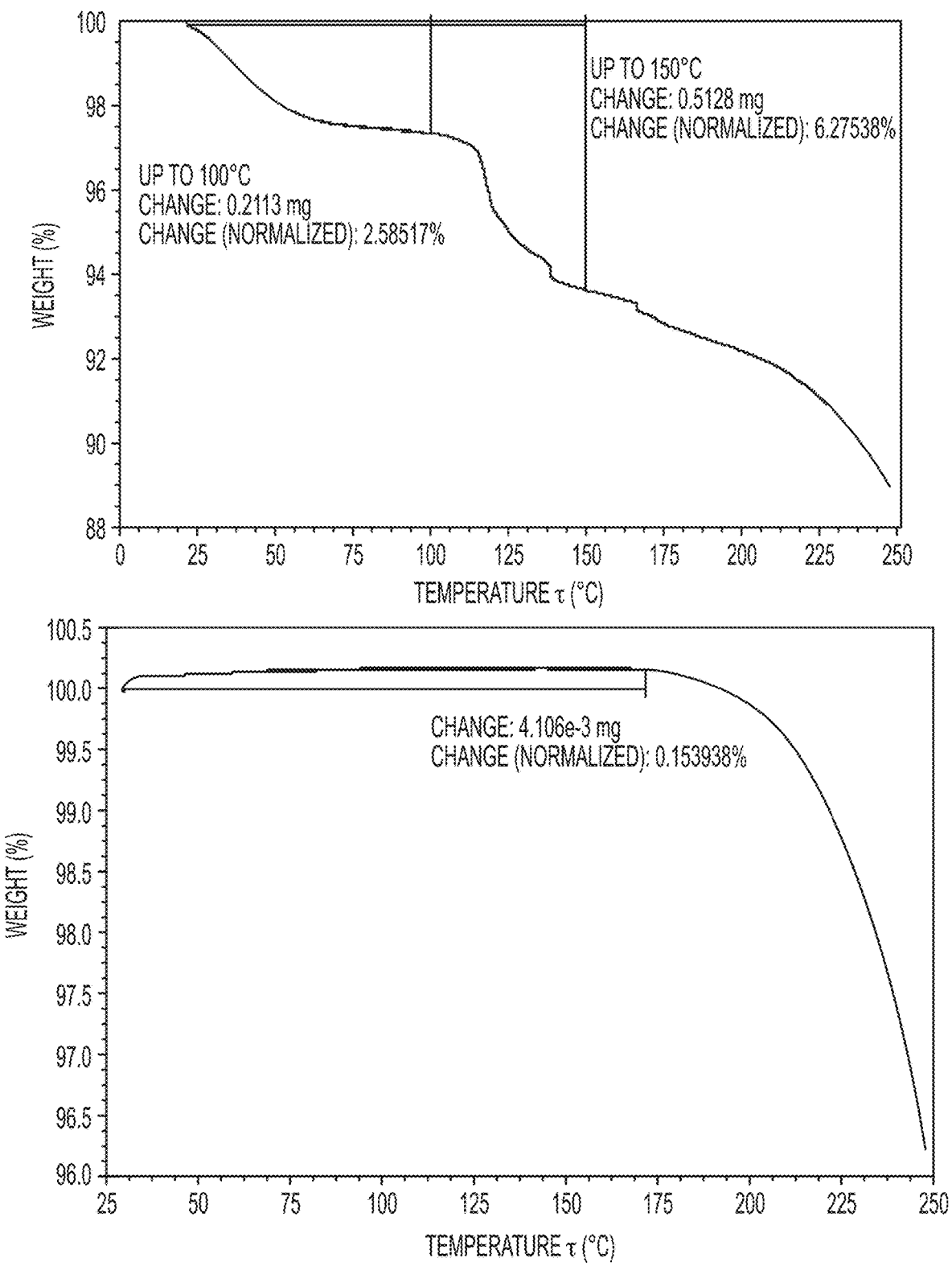
FIG. 8—is a TGA plot of solabegron zwitterion Form II (Top) vs. solabegron zwitterion Form I (bottom)
Figure 9:
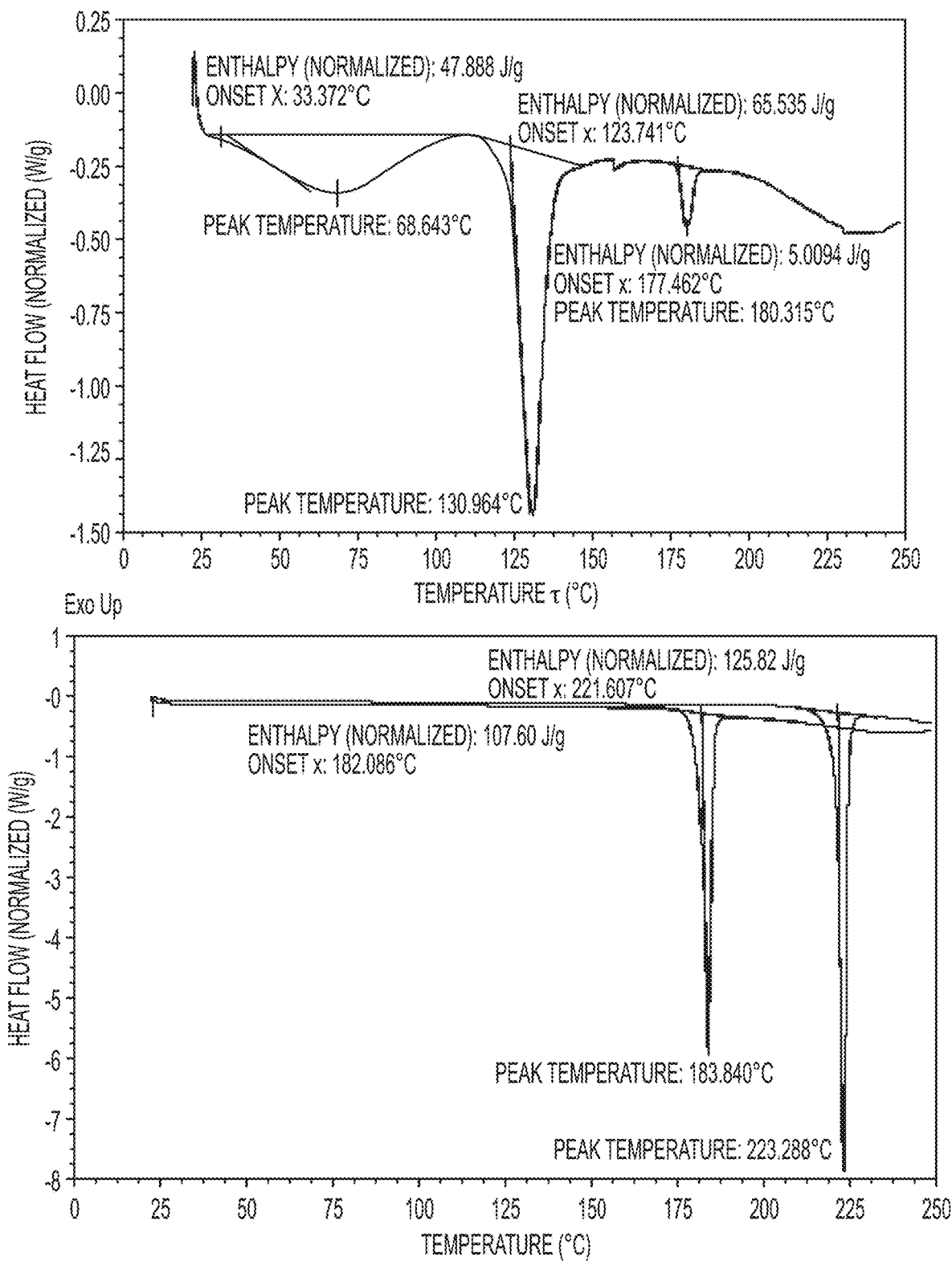
FIG. 9—The top plot is a DSC plot of solabegron zwitterion Form II that reveals three thermal events, peaked around 67° C. (very broad), 131° C. (broad) and 180° C. (narrow), respectively; The bottom plot is a DCS plot of solabegron zwitterion Form I (around 184° C.) and solabegron HCl salt form I (around 223° C.).

The XRPD pattern of the solabegron zwitterion from Procedure A (see FIG. 7), designated as solabegron zwitterion Form II, is distinctly different from the solabegron zwitterion Form I crystal (Form I). FIG. 8 shows the TGA plot of Form II vs. Form I, revealing two steps of wt. losses for Form II, one from 25 to 100° C. by 2.6 wt % and another from 100 to 150° C. by another 3.7 wt %. DSC analysis of solabegron zwitterion Form II, as shown in FIG. 9, reveals three thermal events, peaked around 67° C. (very broad), 131° C. (broad) and 180° C. (narrow), respectively. Correlating with the TGA data, the two events at lower temperatures are likely related to solvent losses.

¹H-NMR and KF analyses of solabegron zwitterion from Procedure A sample gave 2.8 wt % $H_2O$ and 4.3 wt % IPA, respectively. The data approximate the wt % losses by TGA analysis (i.e., 2.6 wt % and 3.7 wt %, respectively).

The relative stability of solabegron zwitterion Forms I and II was evaluated via slurry conditioning of either solabegron zwitterion Form I or a mixture of solabegron zwitterion Forms I and II in IPA/$H_2O$ with different ratio, for a) confirmation of relative stability of the two solabegron zwitterion forms, and b) rational process design and control. The table in FIG. 10 lists the testing conditions and results. Solabegron zwitterion Form II resulted from all tested conditions starting with either solabegron zwitterion Form I alone or a mixture of solabegron zwitterion Forms I and II, indicating solabegron zwitterion Form II is more stable than solabegron zwitterion Form I. This supports that solabegron zwitterion Form II should be the targeted polymorph of isolation for robust purity control of the product.

Procedure C: Solabegron-Zwitterion Crystallization

Solabegron-Na stock solution (50.46 g, 12.8 wt % in 1:1 v/v IPA/water) was charged into a 100 mL vessel; 12 mL 1:1 v/v IPA/water was added and the reaction mixture was heated to 55° C. over 20 min. 2N HCl (12 mL, in 1:1 v/v IPA/water) was added via a dosing unit over 120 min at 55° C. HCl addition was paused when the pH reached 7.0 (total 14.9 mL HCl added). Solabegron zwitterion (form II) seed (3%, 194 mg, 596-172) was added in one portion, and seed bed gradually formed. The thin slurry was aged at 55° C. for 30 min, and the pH went up to 7.3 to 7.5 during this period. HCl was added continuously until a pH of 6.8 was reached (total 2.3 mL 2N HCl added over 23 min). HCl addition was stopped and the slurry was aged at 55° C. for 30 min. The mixture was cooled to 20° C. over 5 h. then aged at 20° C. for 2 h. 2N HCl (1.0 mL) was added over 10 min at 20° C. and the slurry was aged at 20° C. for 5-15 h. The pH was adjusted to 6.8-7.2 (if pH>7.2) by adding slightly more 2N HCl (amount depending on the pH) over 5-30 min. The slurry was aged at 20° C. for 1-5 h. Solid solabegron zwitterion was isolated by filtration. The cake was washed with 20:80 v/v IPA/water 1×25 mL, followed by water 2×25 mL. The solid was then dried under vacuum at 25° C. for 3 h. The solid gave 99.43 LCAP by HPLC.

Example 3: Preparation of the Solabegron HCl Salt (Formula I-HCl)

Procedure A

Solabegron zwitterion solid (4.81 g, 87.6 wt %, equivalent to 4.21 g pure) was mixed with degassed IPA (21 mL) and degassed HPLC water (19.4 mL), in an EasyMax 100 mL vessel. The mixture was heated to 65° C., and 6N HCl (1 equiv) was added in one portion to dissolve all the solid. The ratio of IPA to water was 1:1 v/v. The solution was then cooled to 55° C., 2% seeding (84 mg) was applied by adding the seed in one portion. After aging at 55° C. for 30 min, the resulting mixture was cooled to 0° C. over 5 h, and held at 0° C. for 15 h. The slurry sample was an agglomerate of fine particles by PLM. The solid was isolated by filtration, the wet cake was washed with 20:80 v/v IPA/water 1×20 mL, and water 2×20 mL. The wet cake, as beige solid, gave 99.1 A % by LC (MR325, 242 nm) of solabegron HCl salt.

Procedure B

Figure 11:
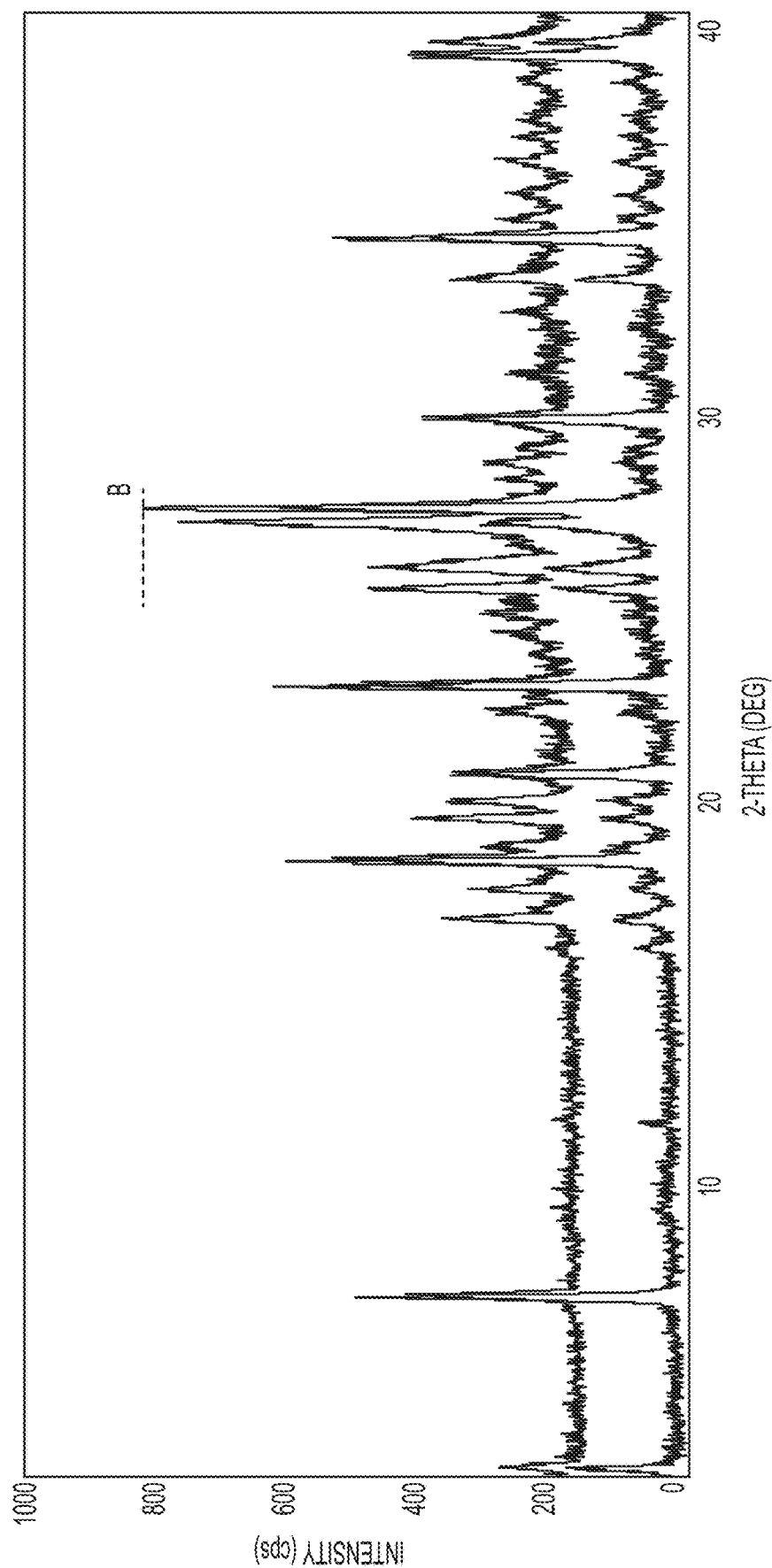

Well purified solabegron zwitterion Form II with 99.4 A % purity LC was converted into solabegron HCl salt. The experiment was carried out at 5 g-solabegron zwitterion scale in a 100 mL EasyMax vessel. The solabegron zwitterion solids were dissolved readily at 68° C. after 6N HCl (~1.05 equiv) was charged. Seed (2%, 100 mg, HCl salt Form I) was added in one portion and a slurry was generated instantly. The batch slurry was cooled to 0° C. over 5 h. After the batch was aged at 0° C. for 8-12 h (overnight), the product was isolated by filtration. The dried product gave 99.8 A % by LC (MR325). The solid was confirmed as Form I by XRPD (FIG. 11), with crystal morphology similar to previous HCl salt by PLM (see FIG. 12). The results from different purity of solabegron zwitterion indicated that as long as zwitterion purity is high enough the existing process for HCl salt crystallization works quite well (with no obvious issue).

Procedure C

An EasyMax 100 mL crystallizer with baffle, was charged with solabegron zwitterion (Form II, 4.71 g=4.0 g pure, 9.73 mmol, 99.0 LCAP), IPA (20 mL), and water (18.4 mL, Chromasolv for HPLC) at ambient temperature. The agitation rate was set to 300 rpm. The reaction mixture, as slurry, was heated to 68-70° C. over 30 min. HCl (6 N, 1.95 mL, 1.2 equiv) was added at 68-70° C. in one portion. The reaction mixture turned a clear solution, pH was 0.3-0.4 at 69° C. The reaction mixture was cooled to 62° C. over 20-30 min. and remained as most clear solution. The batch turned to a slurry and the agitation was set to 500 rpm. Solabegron HCl salt seed (20 mg) was added in one portion. After the batch was aged at 62° C. for 15-20 min, the resulting slurry was cooled to 0° C. over 5 h linearly; and PLM was checked during cooling. The reaction mixture was aged at 0° C. overnight. A slurry sample was taken for PLM, the reaction mixture was at a pH of 2.3. The product was isolated by filtration, the wet cake was washed by 9:1 v/v water/IPA (1×15 mL), followed by water (2×15 mL). After drying at RT with vacuum suction for 3 h, the partially dried solid was further dried in vacuum oven (50° C.) with nitrogen sweep for 20 h. Solabegron-HCl (Formula II) was obtained as off-white solid (4.32 g) in 93.8% isolated yield after subtracting seed.

Example 4: Initial Preparation of the Solabegron Zwitterion Form I

To a 250 mL reactor was added imidazoline IV (46.96 g) in toluene (180 mL). The resulting solution was heated to 55° C. and (R)-2-(3-clorophenyl)oxirane (22.69 g) was added with stirring. The reaction mixture was heated to 120° C. for 26 h. The reaction mixture was cooled to 83° C. and transferred to a 1 L reactor. Isopropyl alcohol (203 mL) and water (203 mL) were added to the reactor. Aqueous sodium hydroxide (42.5 mL, 32% wt./wt.) was added at a temperature above 60° C. The reaction mixture was distilled to remove toluene. IPA (140 mL) was added to the reactor and the reaction mixture was filtered through a carbon disk. Concentrated HCl (18.8 mL) was added to crystallize the zwitterion, which was washed with water (2×90 mL) and IPA (1×90 mL) with vacuum filtration to yield 36.32 g (76%) of small crystals that were confirmed by spectroscopy and XRPD to be the desired solabegron zwitterion. See FIG. 13.

Although the present disclosure has been described in considerable detail with reference to certain preferred versions thereof, other versions are possible. Therefore, the spirit and scope of the application should not be limited to the description of the preferred versions described herein.

All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features. Various modifications of the application, in addition to those described herein, will be apparent to those skilled in the art from the foregoing description. Such modifications are also intended to fall within the scope of the appended claims.

Throughout the above specification a number of references have been cited and or referred to it is to be understood that unless specifically noted, all references cited in the above specification and or referred to in the above specification are hereby incorporated by reference in their entirety.

What is claimed is:

1. An isolated compound according to Formula II:

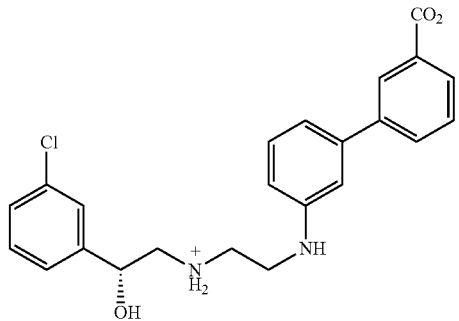

or a pharmaceutically acceptable salt or stereoisomer thereof, in the form of a hydrated isopropanol solvate.

2. The isolated compound according to claim 1, wherein the isolated compound is a crystalline solid.

3. The isolated compound according to claim 1, wherein the compound is at least about 97.0% by weight pure.

4. The isolated compound according to claim 1, wherein the compound is at least about 99.0% by weight pure.

5. The isolated compound according to claim 1, wherein the compound is at least about 99.5% by weight pure.

6. The isolated compound according to claim 1, wherein the compound is at least about 99.9% by weight pure.

7. The isolated compound according to claim 1, wherein no single impurity is present in an amount greater than about 0.5% by weight.

8. The isolated compound according to claim 1, wherein no single impurity is present in an amount greater than about 0.25% by weight.

9. The isolated compound according to claim 1, wherein no single impurity is present in an amount greater than about 0.10% by weight.

10. The compound of claim 1 wherein the hydrated isopropanol solvate is 3 equivalents of the compound of Formula II:1 equivalent of isopropanol:2 equivalents water.

11. A pharmaceutical composition comprising: a therapeutically effective amount of a solid compound according to Formula II:

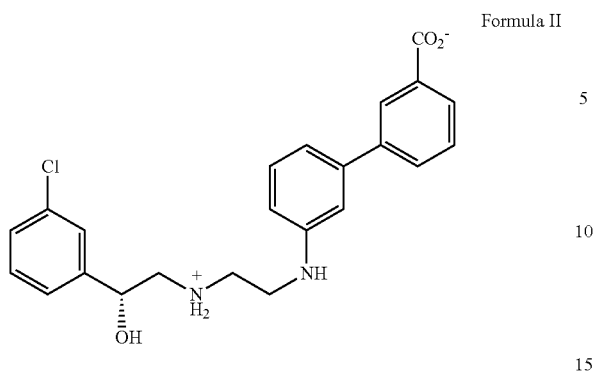

Formula II or a pharmaceutically acceptable salt or stereoisomer, in the form of a hydrate of isopropanol solvate; and at least one pharmaceutically acceptable carrier or excipient.

12. The composition according to claim 11, further comprising one or more additional therapeutic agents selected from the group consisting of: antimuscarinic agents; alpha adrenoceptor blockers; 5-alpha reductases; and phosphodiesterases-5 inhibitors.

13. The pharmaceutical composition of claim 11 wherein the hydrated isopropanol solvate is 3 equivalents of the compound of Formula II:1 equivalent of isopropanol:2 equivalents water.

* * * * *